United States Patent
Pollock et al.

(10) Patent No.: US 10,143,704 B2
(45) Date of Patent: Dec. 4, 2018

(54) METHODS FOR TREATING CANCER

(71) Applicant: Epizyme, Inc., Cambridge, MA (US)

(72) Inventors: Roy M. Pollock, Medford, MA (US); Scott R. Daigle, Newburyport, MA (US); Eric Hedrick, Summit, NJ (US); Nigel Waters, Belmont, MA (US); Blythe Thomson, Newton, MA (US)

(73) Assignee: Epizyme, Inc., Cambridge, MA (US)

( * ) Notice: Subject to any disclaimer, the term of this patent is extended or adjusted under 35 U.S.C. 154(b) by 0 days.

(21) Appl. No.: 15/036,544

(22) PCT Filed: Nov. 13, 2014

(86) PCT No.: PCT/US2014/065517
§ 371 (c)(1),
(2) Date: May 13, 2016

(87) PCT Pub. No.: WO2015/073706
PCT Pub. Date: May 21, 2015

(65) Prior Publication Data
US 2016/0296548 A1  Oct. 13, 2016

Related U.S. Application Data

(60) Provisional application No. 62/075,672, filed on Nov. 5, 2014, provisional application No. 61/992,792, filed on May 13, 2014, provisional application No. 61/903,912, filed on Nov. 13, 2013.

(51) Int. Cl.
*A61K 31/7076* (2006.01)
*C07H 19/16* (2006.01)

(52) U.S. Cl.
CPC ......... *A61K 31/7076* (2013.01); *C07H 19/16* (2013.01)

(58) Field of Classification Search
CPC ............................ A61K 31/7076; C07H 19/16
See application file for complete search history.

(56) References Cited

U.S. PATENT DOCUMENTS

2012/0142625 A1* 6/2012 Olhava ................ C07D 487/04
514/46

FOREIGN PATENT DOCUMENTS

WO  WO 2012/075500 A2  6/2012

OTHER PUBLICATIONS

Daigle et al., Blood, 2013, 122(6), p. 1017-1025, Prepublished online as Blood First Edition paper, Jun. 25, 2013.*
Pollock et al., Blood, 2012, 120, p. 2379, 54th ASH Annual Meeting Abstract, meeting held Dec. 8-11, 2012.*
Daigle et al., Cancer Cell, 2011, 20, p. 53-65.*
Rubnitz et al., Blood, 2009, 113(21), p. 5083-5089. (Year: 2009).*
Reagan-Shaw et al., "Dose translation from animal to human studies," *The FASEB Journal*, 2008, vol. 22(3), pp. 659-661.

* cited by examiner

*Primary Examiner* — Jonathan S Lau
(74) *Attorney, Agent, or Firm* — Cooley LLP; Heidi A. Erlacher; Xixi Sun

(57) ABSTRACT

The present invention relates to DOT1L inhibitors. The present invention also relates to pharmaceutical compositions containing these compounds and methods of treating disorders in which DOT1-mediated protein methylation plays a part, such as cancer, by administering these compounds and pharmaceutical compositions to subjects in need thereof.

19 Claims, 8 Drawing Sheets

Figure 1: Phase 1 Dose Escalation Summary

High favorable safety profile, treatment effects observed among MLL-r patients

- *Four dose cohorts have been completed (12, 24, 36 and 54mg/m2)*
  - Dosing schedule: 21 day continuous IV infusion, 7 day drug holiday per cycle
  - 16 total patients, 9 patients with MLL-r (8 acute leukemia, one CMML)
  - Fifth cohort (80mg/m2) beginning enrollment

- *Tolerability and safety profile has been highly favorable*
  - No DLTs, drug-related treatment discontinuations, or apparent dose: toxicity relationship
  - Ability to continue to escalate dose in expansion cohort

- *Treatment effects observed in 4 of 8 acute leukemia MLL-r patients*
  - No effects seen in non MLL-r patients

- *Pharmacokinetics: dose-proportional exposure*

- *Pharmacodynamics: methyl mark reduction is dose- and time-dependent*

- *Initiating MLL-r expansion stage with continuous administration*
  - Starting dose in expansion cohort 80mg/m2
  - Safety profile and study design allow for continued dose escalation if indicated

Figure 2: Genetically Defined Acute Leukemias

| | MLL-r | MLL-PTD |
|---|---|---|
| Genetic Alteration | • Reciprocal chromosomal translocations involving 11q23 | • Partial duplication of MLL gene |
| Disease | • 5-10% AML and ALL<br>• In adults and pediatrics<br>• 4,900 annual incidence in major markets | • 5-8% of AML in adults<br>• 1,700 annual incidence in major markets |
| Diagnostic Test | • Cytogenetics, FISH<br>• Currently performed in all acute leukemia patients | • PCR<br>• Research test in selected patients |
| Prognostic implications | • Poor DFS and OS compared with non MLL-r leukemias | • Short remission duration with SOC therapy |

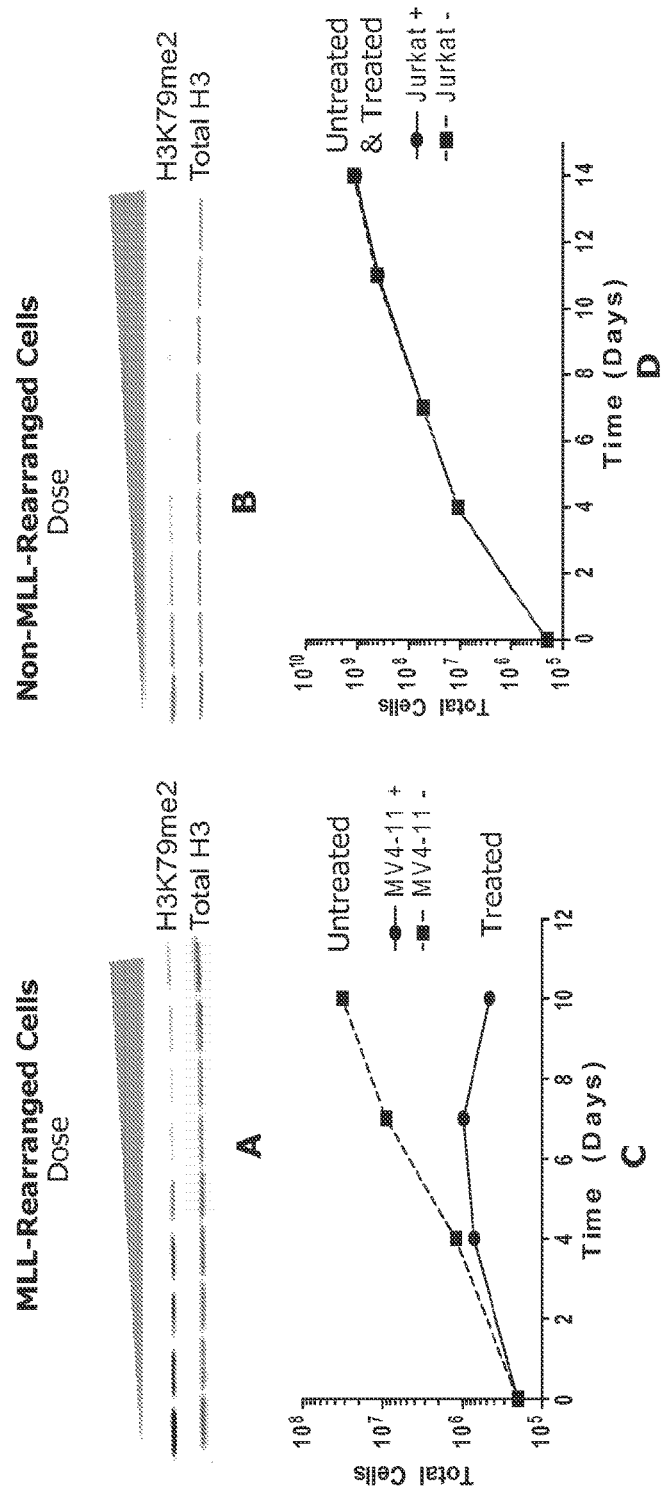

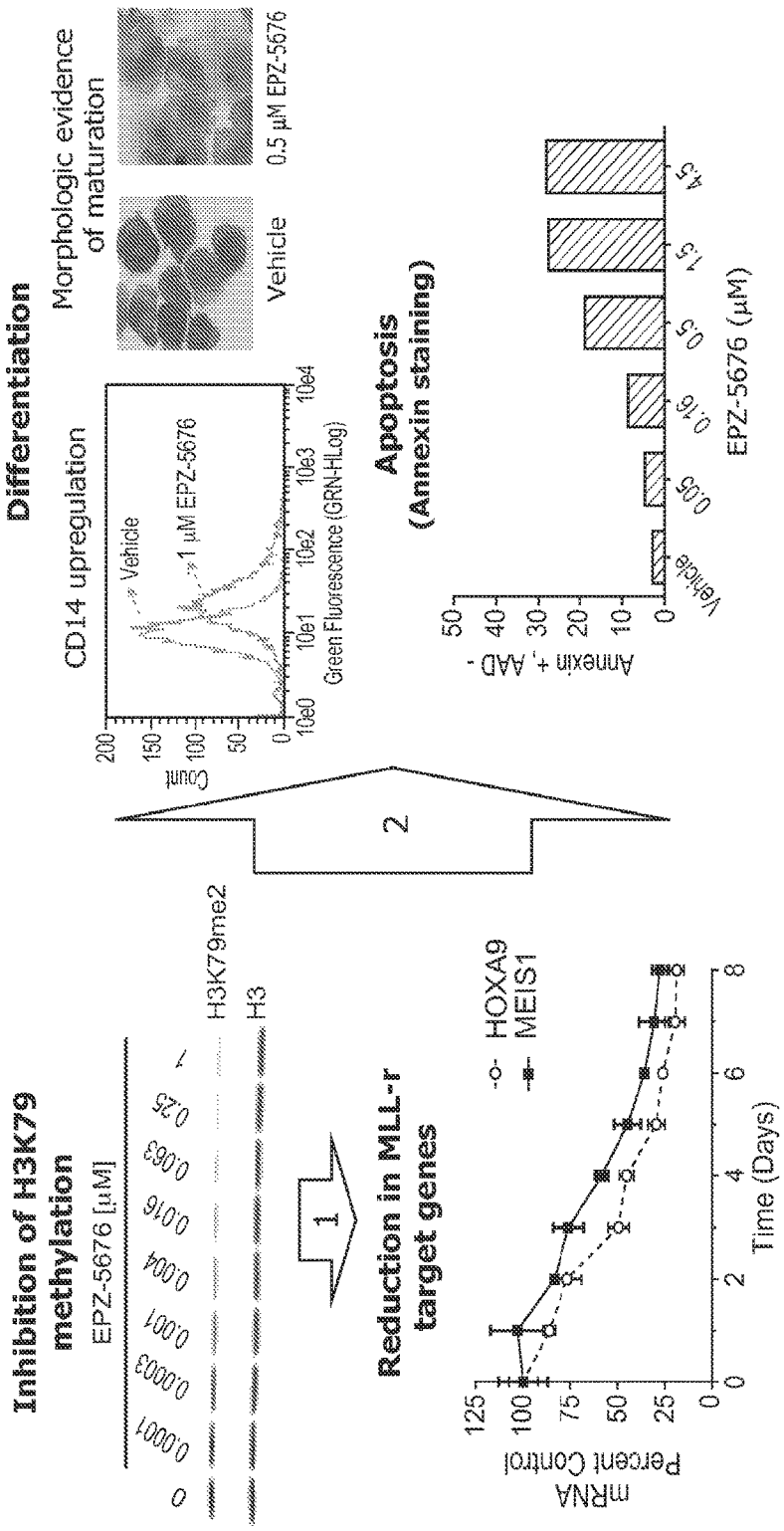

Figure 5: EPZ-5676 Dose Escalation Demographics

- Four dose cohorts have been completed (12, 24, 36 and 54 mg/m2)
  - Heavily pretreated population
  - 16 patients, 8 acute leukemias with MLL-r
- Dosing schedule: 21-day continuous IV infusion, 7-day drug holiday per cycle
- Enrolling fifth cohort (80mg/m2)

| | |
|---|---|
| Age Median (range) | 55 (22-81) |
| Gender | Male 11<br>Female 5 |
| Diagnosis | AML 13 (7 MLL-r)<br>ALL 1 (MLL-r)<br>ALL (Ph+) 1<br>CMML 1 (MLL-r) |
| # Prior Therapies Median (range) | 4 (1-8) |
| Prior Allogeneic SCT | Yes 6<br>No 10 |

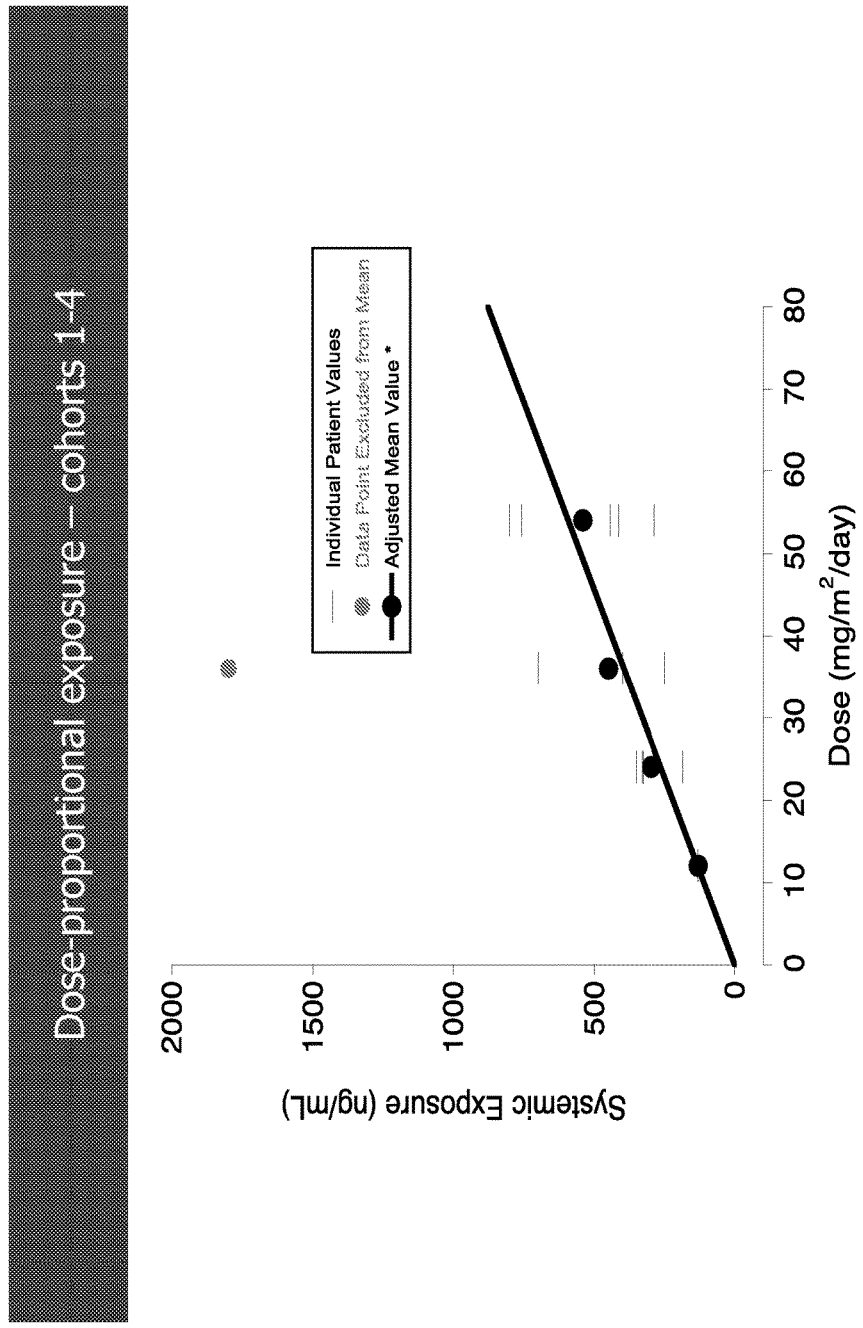
Figure 6: EPZ-5676 Dose Escalation – PK Summary

Figure 7: EPZ-5676 Dose Escalation – MLL-r Patient Summary

| Cohort Dose | Dx | MLL-r t(11q23) | H3K79 Me Inhibition (%) | Anti-Leukemic Effects | Outcome |
|---|---|---|---|---|---|
| 2 (24 mg/m²) | ALL | (4;11) | 60 | PB 90% blast reduction<br>Resolution of fevers | PD (C1) |
| | AML | (6;11) | 0 | None observed | PD (C1) |
| 3 (36 mg/m²) | AML | (11;19) | 50 | Maturation in PB and marrow (no change % blasts)<br>Leukocytosis<br>Resolution of cachexia | PD (C3) |
| | AML | (6;11) | 80 | Maturation in PB (no change % blasts)<br>Leukocytosis<br>Resolution of leukemia cutis | PD (C2) |
| | AML | (3;11) | 60 | None observed | PD (C1) |
| 4 (54 mg/m2) | AML | (11;19) | 40 | None observed | PD (C2) |
| | AML | (11;19) | 60 | Maturation in marrow<br>% marrow blast decrease (20% → 2%) | On study (2nd cycle) |
| | CMML | (11;19) | 40 | Too early to evaluate | On study (2nd cycle) |
| | AML | (6;11) | NE | None observed | PD (C1) |

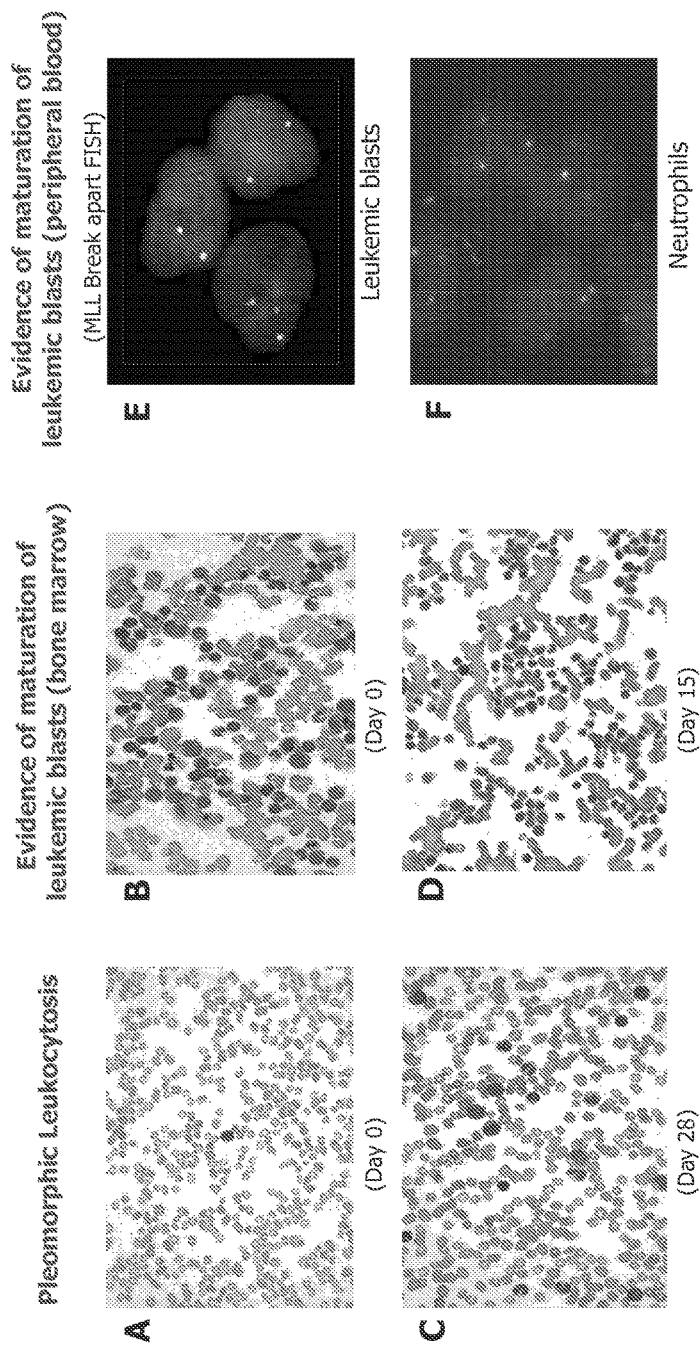

METHODS FOR TREATING CANCER

RELATED APPLICATIONS

This application is a U.S. National Phase application, filed under 35 U.S.C. § 371, of International Application No. PCT/US2014/065517, filed Nov. 13, 2014, which claims priority to and the benefit of the U.S. Provisional Application Nos. 61/903,912 filed Nov. 13, 2013, 61/992,792 filed May 13, 2014, and 62/075,672 filed Nov. 5, 2014, the contents of each of which are hereby incorporated by reference in their entireties.

FIELD OF INVENTION

The present invention relates generally to the field of cancer treatment, and in particular, the treatment of leukemia associated with MLL gene rearrangement. More particularly, the present invention provides methods and compositions which treat, alleviate, prevent, diminish or otherwise ameliorate the symptoms of leukemia associated with MLL gene rearrangement.

BACKGROUND OF THE INVENTION

There is an ongoing need for new agents which modulate the aberrant action of epigenetic enzymes.

SUMMARY OF THE INVENTION

The present invention provides a method of treating leukemia by administering to a subject in need thereof a therapeutically effective amount of a compound of Formula (I) or its N-oxide or a pharmaceutically acceptable salt thereof:

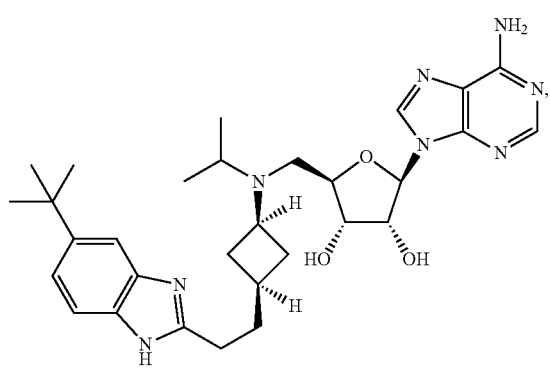

(I)

where the compound of Formula (I) or its N-oxide or a pharmaceutically acceptable salt thereof is administered continuously for at least 7, 14, 21, 28, 35, 42, 47, 56, or 64 days. As used herein, the expressions "compound of Formula (I)," "Compound A2," and "EPZ-5676" all refer to the same compound and can be used interchangeably.

In certain embodiments, the continuous administration is an administration without a drug holiday. For example, the compound of Formula (I) or its N-oxide or a pharmaceutically acceptable salt thereof is administered continuously, e.g., via intravenous ("IV") infusion, for 28 days in a 28-day cycle.

In some embodiments, the compound is administered with a drug holiday. For example, the compound of Formula (I) or its N-oxide or a pharmaceutically acceptable salt thereof is administered, e.g., via IV infusion, for 21 days of a 28-day cycle with a 7-day drug holiday per cycle.

In certain embodiments, continuous administration results in reduction of H3K79 methyl mark to at least 90%, 80%, 70%, 60%, 50%, 40%, 30%, 20%, 10% or less of untreated control levels.

In certain embodiments, continuous administration results in the suppression of H3K79 methyl mark rebound.

The present invention also provides a method of treating leukemia by administering to a subject in need thereof a therapeutically effective amount of a compound of Formula (I) or its N-oxide or a pharmaceutically acceptable salt thereof:

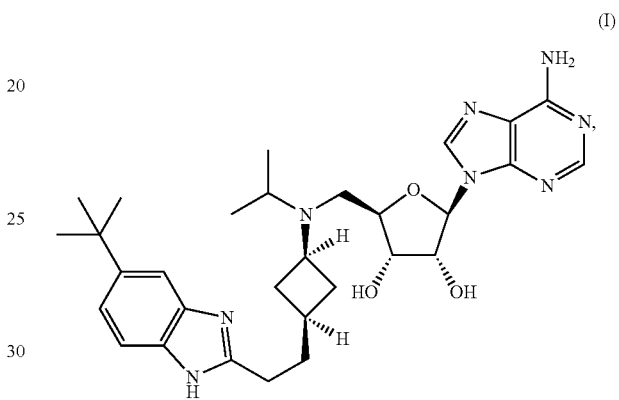

(I)

where the compound of Formula (I) or its N-oxide or a pharmaceutically acceptable salt thereof is administered at a dose of at least 12 mg/m²/day, 24 mg/m²/day, 36 mg/m²/day, 45 mg/m²/day, 54 mg/m²/day, 70 mg/m²/day, 80 mg/m²/day, or 90 mg/m²/day.

In certain embodiments, in any method described herein, the compound of Formula (I) or its N-oxide or a pharmaceutically acceptable salt thereof is administered at a dose of at least 12 mg/m²/day.

In certain embodiments, in any method described herein, the compound of Formula (I) or its N-oxide or a pharmaceutically acceptable salt thereof is administered at a dose of at least 24 mg/m²/day.

In certain embodiments, in any method described herein, the compound of Formula (I) or its N-oxide or a pharmaceutically acceptable salt thereof is administered at a dose of at least 45 mg/m²/day.

In certain embodiments, in any method described herein, the compound of Formula (I) or its N-oxide or a pharmaceutically acceptable salt thereof is administered at a dose of at least 54 mg/m²/day.

In certain embodiments, in any method described herein, the compound of Formula (I) or its N-oxide or a pharmaceutically acceptable salt thereof is administered at a dose of at least 70 mg/m²/day.

In certain embodiments, in any method described herein, the compound of Formula (I) or its N-oxide or a pharmaceutically acceptable salt thereof is administered at a dose of at least 80 mg/m²/day.

In certain embodiments, in any method described herein, the compound of Formula (I) or its N-oxide or a pharmaceutically acceptable salt thereof is administered at a dose of at least 90 mg/m²/day.

In certain embodiments, in any method described herein, the compound of Formula (I) or its N-oxide or a pharmaceutically acceptable salt thereof is administered at a dose of at least 12 mg/m²/day, 24 mg/m²/day, 36 mg/m²/day, 45 mg/m²/day, 54 mg/m²/day, 70 mg/m²/day, 80 mg/m²/day, or 90 mg/m²/day.

In certain embodiments, in any method described herein, the compound of Formula (I) or its N-oxide or a pharmaceutically acceptable salt thereof is administered at a dose of at least 45 mg/m²/day (e.g., about 45 mg/m²/day, about 50 mg/m²/day, about 55 mg/m²/day, about 60 mg/m²/day, about 65 mg/m²/day, about 70 mg/m²/day, about 75 mg/m²/day, about 80 mg/m²/day, about 85 mg/m²/day, about 90 mg/m²/day, about 95 mg/m²/day or about 100 mg/m²/day) to a subject younger than 12 months (e.g., between 3-12 months old).

In certain embodiments, in any method described herein, the compound of Formula (I) or its N-oxide or a pharmaceutically acceptable salt thereof is administered at a dose of at least 70 mg/m²/day (e.g., about 70 mg/m²/day, about 75 mg/m²/day, about 80 mg/m²/day, about 85 mg/m²/day, about 90 mg/m²/day, about 95 mg/m²/day or about 100 mg/m²/day) to a subject older than 12 months but younger than 18 years old.

In certain embodiments, in any method described herein, the compound of Formula (I) or its N-oxide or a pharmaceutically acceptable salt thereof is administered at a dose of at least 90 mg/m²/day (e.g., about 90 mg/m²/day, about 95 mg/m²/day or about 100 mg/m²/day) for an adult subject (e.g., subject aged 18 years or older).

The present invention further provides a method of treating leukemia by administering to a subject in need thereof a therapeutically effective amount of a compound of Formula (I) or its N-oxide or a pharmaceutically acceptable salt thereof:

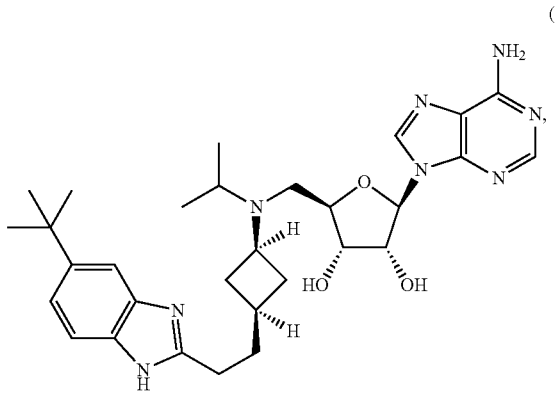
(I)

where the administration results in maturation or differentiation of leukemic blast cells.

In certain embodiments, at least 20% of leukemic blast cells have undergone maturation or differentiation.

In certain embodiments, at least 50% of leukemic blast cells have undergone maturation or differentiation.

In certain embodiments, at least 80% of leukemic blast cells have undergone maturation or differentiation.

The present invention also provides a method for inducing leukemic blast cell maturation or differentiation by administering to a patient in need thereof an effective amount of compound of Formula (I)

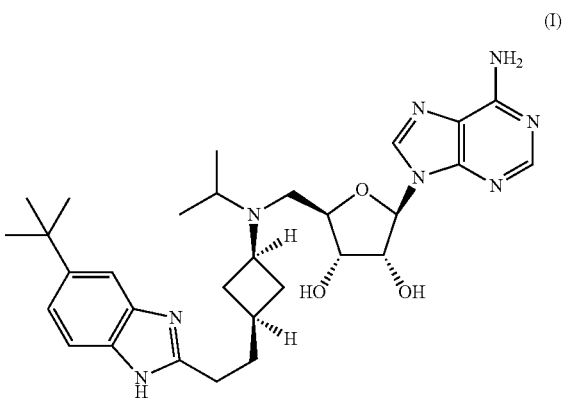 [SMILES: CC(C)N(C[C@H]1O[C@@H](n2cnc3c(N)ncnc32)[C@H](O)[C@@H]1O)[C@H]1C[C@@H](CCc2nc3cc(C(C)(C)C)ccc3[nH]2)C1]
(I)

or its N-oxide or a pharmaceutically acceptable salt thereof.

In certain embodiments, at least 20%, 30%, 40%, 50%, 60%, 70%, 80%, or 90% of the leukemic blast cells undergo maturation or differentiation.

In any method described herein, the compound of Formula (I) or its N-oxide or a pharmaceutically acceptable salt thereof can be administered at a dose of at least 12 mg/m²/day, at least 24 mg/m²/day, at least 36 mg/m²/day, at least 45 mg/m²/day, at least 54 mg/m²/day, at least 70 mg/m²/day, at least 80 mg/m²/day, or at least 90 mg/m²/day.

In certain embodiments, in any method described herein, the subject is an adult patient aged 18 years or older.

In certain embodiments, in any method described herein, the subject is a pediatric patient aged 12 months or younger (e.g., between 3 and 12 months old).

In certain embodiments, in any method described herein, the subject is a subject older than 12 months but younger than 18 years old.

In any method described herein, the administration of the compound of Formula (I) or its N-oxide or a pharmaceutically acceptable salt thereof results in maturation or differentiation of leukemic blast cells and at least 20%, 50% or 80% of leukemic blast cells have undergone maturation or differentiation.

In any method described herein, at least 20%, 30%, 40%, 50%, 60%, 70%, 80%, or 90% of the leukemic blast cells undergo cell death or apoptosis.

In any method described herein, the subject can be a pediatric (non-adult) patient aged 3 months to 18 years.

In any method described herein, the leukemia is chronic myelomonocytic leukemia (CMML), acute myeloid leukemia (AML), acute lymphoid leukemia (ALL), acute mixed lineage leukemia, myelodysplastic syndrome, myeloproliferative neoplasia (MPN) or leukemia characterized by MLL gene rearrangement (e.g., MLL-r or partial tandem duplication of MLL (MLL-PTD)).

For example, the MLL gene rearrangement is translocation of the MLL gene 11q23.

For example, the MLL gene rearrangement is partial tandem duplication of the MLL gene.

For example, the MLL gene rearrangement results in increased or errand DOT1L methylation activity.

In yet another aspect, the present invention provides a method for assessing the efficacy of the compound described herein. The method includes administering to a subject suffering from leukemia an amount of a compound of Formula (I) or its N-oxide or a pharmaceutically acceptable salt thereof to determine if the amount administered is therapeutically efficient.

Any method presented herein includes resolution of fevers, resolution of cachexia or resolution of leukemia cutis.

Any method presented herein results in restoration of normal haematopoiesis.

BRIEF DESCRIPTION OF THE DRAWINGS

FIG. 1 is a summary of Phase 1 dose escalation study of EPZ-5676.

FIG. 2 is a summary of certain characterizations of MLL-r and MLL-PTD.

FIGS. 3A-3D are pre-clinical study plots of EPZ-5676 demonstrating that target methyl mark inhibition leads to selective killing of genetically defined cancer cells, e.g., MLL-r cells.

FIG. 4 is a proposed mechanism of action based on pre-clinical study of EPZ-5676.

FIG. 5 is a summary of demographic information for Phase 1 dose escalation study of EPZ-5676.

FIG. 6 is a pharmacokinetics (PK) plot from Phase 1 dose escalation study of EPZ-5676.

FIG. 7 is a summary of patients treated in the Phase 1 dose escalation study of EPZ-5676. "PD" means progressive disease and "C" means cycle.

FIGS. 8A-8F are series of micrographs demonstrating that EPZ-5676 treatment leads to a differentiation effect in patients with MLL-r.

DETAILED DESCRIPTION OF THE INVENTION

One aspect of the present invention is based in part upon the discovery that DOT1L inhibitors can effectively treat leukemia that is characterized by MLL gene rearrangement by inducing maturation or differentiation of leukemic blast cells (as shown by the data in Appendix 1 of U.S. Provisional Application Ser. No. 61/903,912 filed Nov. 13, 2013, the content of which is incorporated herein by reference in its entirety). In certain embodiments the maturation or differentiation of leukemic blast cells is followed by cell death and/or apoptosis of the differentiated blast cells.

One aspect of the invention comprises continuous administration of a DOT1L inhibitor to a subject suffering from leukemia. In certain embodiments the continuous administration is for at least 7, 14, 21, 28, 35, 42, 47, 56, 63, 70, or 77 days. In certain embodiments, the continuous administration is an administration without a drug holiday. For example, the DOT1L inhibitor, such as the compound of Formula (I) or its N-oxide or a pharmaceutically acceptable salt thereof, is administered continuously (e.g., by IV infusion) for, e.g., 7 days in a 7-day cycle, 14 days in a 14-day cycle, 28 days in a 28-day cycle, 35 days in a 35-day cycle, etc. In certain embodiments, continuous administration results in reduction of H3K79 methyl mark to at least 90%, 80%, 70%, 60%, 50%, 40%, 30%, 20%, 10% or less of untreated control levels. In certain embodiments, continuous administration results in the suppression of H3K79 methyl mark rebound. In certain embodiments, the DOT1L inhibitor (e.g., the compound of Formula (I) or its N-oxide or a pharmaceutically acceptable salt thereof) is continuously administered at a dose of at least 12 mg/m$^2$/day, 24 mg/m$^2$/day, 36 mg/m$^2$/day, 45 mg/m$^2$/day, 54 mg/m$^2$/day, 70 mg/m$^2$/day, 80 mg/m$^2$/day, or 90 mg/m$^2$/day.

In some embodiments, the compound of Formula (I) or its N-oxide or a pharmaceutically acceptable salt thereof is continuously administered at a dose of 90 mg/m$^2$/day without a drug holiday (e.g., the compound is administered continuously for 28 days in a 28-day cycle).

In some embodiments, the compound of Formula (I) or its N-oxide or a pharmaceutically acceptable salt thereof is continuously administered at a dose of 54 mg/m$^2$/day without a drug holiday (e.g., the compound is administered continuously for 28 days in a 28-day cycle).

In some embodiments, the compound of Formula (I) or its N-oxide or a pharmaceutically acceptable salt thereof is continuously administered at a dose of 80 mg/m$^2$/day without a drug holiday (e.g., the compound is administered continuously for 28 days in a 28-day cycle).

In some embodiments, the DOT1L inhibitor, such as the compound of Formula (I) or its N-oxide or a pharmaceutically acceptable salt thereof, is administered with a drug holiday. For example, the DOT1L inhibitor, such as the compound of Formula (I) or its N-oxide or a pharmaceutically acceptable salt thereof, is administered for, e.g., 21 days of a 28-day cycle with a 7-day drug holiday, 28 days of a 35-day cycle with a 7-day drug holiday, or 21 days of a 35-day cycle with a 14-day drug holiday. In some embodiments, the compound of Formula (I) or its N-oxide or a pharmaceutically acceptable salt thereof is administered with a drug holiday at a dose of at least 12 mg/m$^2$/day, 24 mg/m$^2$/day, 36 mg/m$^2$/day, 45 mg/m$^2$/day, 54 mg/m$^2$/day, 70 mg/m$^2$/day, 80 mg/m$^2$/day, or 90 mg/m$^2$/day. In some embodiments, the compound of Formula (I) or its N-oxide or a pharmaceutically acceptable salt thereof is administered with a drug holiday at a dose of at least 36 mg/m$^2$/day. In some embodiments, the compound of Formula (I) or its N-oxide or a pharmaceutically acceptable salt thereof is administered with a drug holiday at a dose of at least 45 mg/m$^2$/day. In some embodiments, the compound of Formula (I) or its N-oxide or a pharmaceutically acceptable salt thereof is administered with a drug holiday at a dose of at least 54 mg/m$^2$/day. In some embodiments, the compound of Formula (I) or its N-oxide or a pharmaceutically acceptable salt thereof is administered with a drug holiday at a dose of at least 70 mg/m$^2$/day. In some embodiments, the compound of Formula (I) or its N-oxide or a pharmaceutically acceptable salt thereof is administered with a drug holiday at a dose of at least 80 mg/m$^2$/day.

In some embodiments, the compound of Formula (I) or its N-oxide or a pharmaceutically acceptable salt thereof is administered with a drug holiday at a dose of at least 90 mg/m$^2$/day (e.g., administered for 21 days of a 28-day cycle with a 7-day drug holiday).

In some embodiments, the compound of Formula (I) or its N-oxide or a pharmaceutically acceptable salt thereof is administered with a drug holiday at a dose of at least 54 mg/m$^2$/day (e.g., administered for 21 days of a 28-day cycle with a 7-day drug holiday).

In some embodiments, the compound of Formula (I) or its N-oxide or a pharmaceutically acceptable salt thereof is administered with a drug holiday at a dose of at least 80 mg/m$^2$/day (e.g., administered for 21 days of a 28-day cycle with a 7-day drug holiday).

The present invention also provides a method of treating leukemia by administering to a subject in need thereof a therapeutically effective amount of a compound of Formula (I) or its N-oxide or a pharmaceutically acceptable salt thereof:

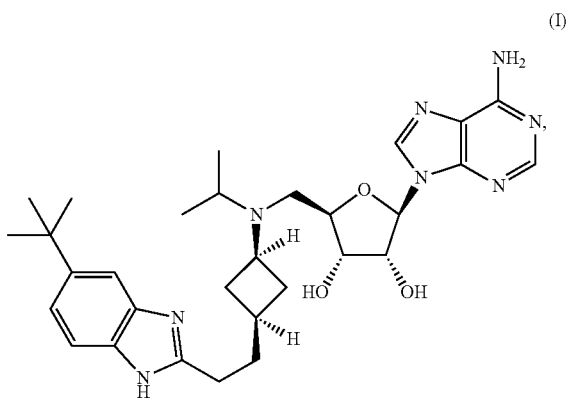 [SMILES: CC(C)N(C[C@H]1O[C@@H](n2cnc3c(N)ncnc32)[C@H](O)[C@@H]1O)[C@H]1C[C@@H](CCc2nc3cc(C(C)(C)C)ccc3[nH]2)C1]

(I)

where the compound of Formula (I) or its N-oxide or a pharmaceutically acceptable salt thereof is administered at a dose of at least 12 mg/m$^2$/day, 24 mg/m$^2$/day, 36 mg/m$^2$/day, 45 mg/m$^2$/day, 54 mg/m$^2$/day, 70 mg/m$^2$/day, 80 mg/m$^2$/day, or 90 mg/m$^2$/day.

In certain embodiments, in any method described herein, the compound of Formula (I) or its N-oxide or a pharmaceutically acceptable salt thereof is administered at a dose of at least 12 mg/m$^2$/day.

In certain embodiments, in any method described herein, the compound of Formula (I) or its N-oxide or a pharmaceutically acceptable salt thereof is administered at a dose of at least 24 mg/m$^2$/day.

In certain embodiments, in any method described herein, the compound of Formula (I) or its N-oxide or a pharmaceutically acceptable salt thereof is administered at a dose of at least 45 mg/m$^2$/day.

In certain embodiments, in any method described herein, the compound of Formula (I) or its N-oxide or a pharmaceutically acceptable salt thereof is administered at a dose of at least 54 mg/m$^2$/day.

In certain embodiments, in any method described herein, the compound of Formula (I) or its N-oxide or a pharmaceutically acceptable salt thereof is administered at a dose of at least 70 mg/m$^2$/day.

In certain embodiments, in any method described herein, the compound of Formula (I) or its N-oxide or a pharmaceutically acceptable salt thereof is administered at a dose of at least 80 mg/m$^2$/day.

In certain embodiments, in any method described herein, the compound of Formula (I) or its N-oxide or a pharmaceutically acceptable salt thereof is administered at a dose of at least 90 mg/m$^2$/day.

In certain embodiments, in any method described herein, the compound of Formula (I) or its N-oxide or a pharmaceutically acceptable salt thereof is administered at a dose of at least 12 mg/m$^2$/day, 24 mg/m$^2$/day, 36 mg/m$^2$/day, 45 mg/m$^2$/day, 54 mg/m$^2$/day, 70 mg/m$^2$/day, 80 mg/m$^2$/day, or 90 mg/m$^2$/day.

In certain embodiments, in any method described herein, the compound of Formula (I) or its N-oxide or a pharmaceutically acceptable salt thereof is administered at a dose of at least 45 mg/m$^2$/day (e.g., about 45 mg/m$^2$/day, about 50 mg/m$^2$/day, about 55 mg/m$^2$/day, about 60 mg/m$^2$/day, about 65 mg/m$^2$/day, about 70 mg/m$^2$/day, about 75 mg/m$^2$/day, about 80 mg/m$^2$/day, about 85 mg/m$^2$/day, about 90 mg/m$^2$/day, about 95 mg/m$^2$/day or about 100 mg/m$^2$/day) to a subject younger than 12 months (e.g., between 3-12 months old). In some embodiments, the compound of Formula (I) or its N-oxide or a pharmaceutically acceptable salt thereof is administered without a drug holiday.

In some embodiments, the compound of Formula (I) or its N-oxide or a pharmaceutically acceptable salt thereof is continuously administered at a dose of 45 mg/m$^2$/day to a subject younger than 12 months (e.g., between 3-12 months old) without a drug holiday (e.g., the compound is administered continuously for 28 days in a 28-day cycle).

In some embodiments, the compound of Formula (I) or its N-oxide or a pharmaceutically acceptable salt thereof is administered at a dose of 45 mg/m$^2$/day to a subject younger than 12 months (e.g., between 3-12 months old) with a drug holiday (e.g., 21 days of a 28-day cycle with a 7-day drug holiday).

In certain embodiments, in any method described herein, the compound of Formula (I) or its N-oxide or a pharmaceutically acceptable salt thereof is administered at a dose of 45 mg/m$^2$/day to a subject younger than 12 months (e.g., between 3-12 months old). In certain embodiments, in any method described herein, the compound of Formula (I) or its N-oxide or a pharmaceutically acceptable salt thereof is administered to a subject younger than 12 months (e.g., between 3-12 months old) at a dose that is 50% of the dose administered to an adult subject. In some embodiments, the compound of Formula (I) or its N-oxide or a pharmaceutically acceptable salt thereof is administered without a drug holiday.

In certain embodiments, in any method described herein, the compound of Formula (I) or its N-oxide or a pharmaceutically acceptable salt thereof is administered at a dose of at least 70 mg/m$^2$/day (e.g., about 70 mg/m$^2$/day, about 75 mg/m$^2$/day, about 80 mg/m$^2$/day, about 85 mg/m$^2$/day, about 90 mg/m$^2$/day, about 95 mg/m$^2$/day or about 100 mg/m$^2$/day) to a subject older than 12 months but younger than 18 years old. In some embodiments, the compound of Formula (I) or its N-oxide or a pharmaceutically acceptable salt thereof is administered without a drug holiday.

In some embodiments, the compound of Formula (I) or its N-oxide or a pharmaceutically acceptable salt thereof is continuously administered at a dose of 70 mg/m$^2$/day to a subject older than 12 months but younger than 18 years old without a drug holiday (e.g., the compound is administered continuously for 28 days in a 28-day cycle).

In some embodiments, the compound of Formula (I) or its N-oxide or a pharmaceutically acceptable salt thereof is administered at a dose of 70 mg/m$^2$/day to a subject older than 12 months but younger than 18 years old with a drug holiday (e.g., 21 days of a 28-day cycle with a 7-day drug holiday).

In certain embodiments, in any method described herein, the compound of Formula (I) or its N-oxide or a pharmaceutically acceptable salt thereof is administered at a dose of 70 mg/m$^2$/day to a subject older than 12 months but younger than 18 years old. In certain embodiments, in any method described herein, the compound of Formula (I) or its N-oxide or a pharmaceutically acceptable salt thereof is administered to a subject older than 12 months but younger than 18 years old. at a dose that is 80% of the dose administered to an adult subject. In some embodiments, the compound of Formula (I) or its N-oxide or a pharmaceutically acceptable salt thereof is administered without a drug holiday.

In certain embodiments, in any method described herein, the compound of Formula (I) or its N-oxide or a pharmaceutically acceptable salt thereof is administered at a dose of at least 90 mg/m$^2$/day (e.g., about 90 mg/m$^2$/day, about 95 mg/m$^2$/day or about 100 mg/m$^2$/day) for an adult subject (a subject aged 18 years or older).

The present invention further provides a method of treating leukemia by administering to a subject in need thereof a therapeutically effective amount of a compound of Formula (I) or its N-oxide or a pharmaceutically acceptable salt thereof:

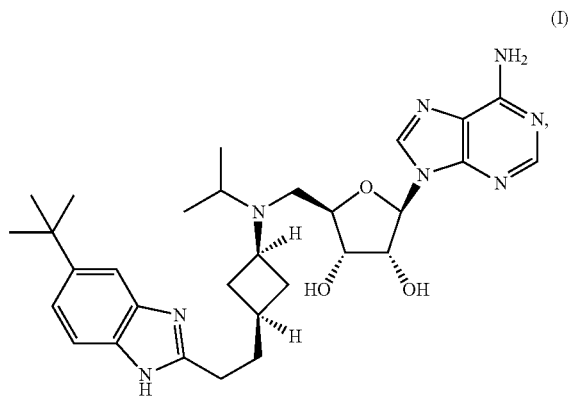 [SMILES: CC(C)N(C[C@H]1O[C@@H](n2cnc3c(N)ncnc32)[C@H](O)[C@@H]1O)[C@H]1C[C@@H](CCc2nc3cc(C(C)(C)C)ccc3[nH]2)C1]

(I)

where the administration results in maturation or differentiation of leukemic blast cells. In certain embodiments, at least 20% of leukemic blast cells have undergone maturation or differentiation. In certain embodiments, at least 50% of leukemic blast cells have undergone maturation or differentiation. In certain embodiments, at least 80% of leukemic blast cells have undergone maturation or differentiation.

The present invention also provides a method for inducing leukemic blast cell maturation or differentiation by administering to a patient in need thereof an effective amount of compound of Formula (I)

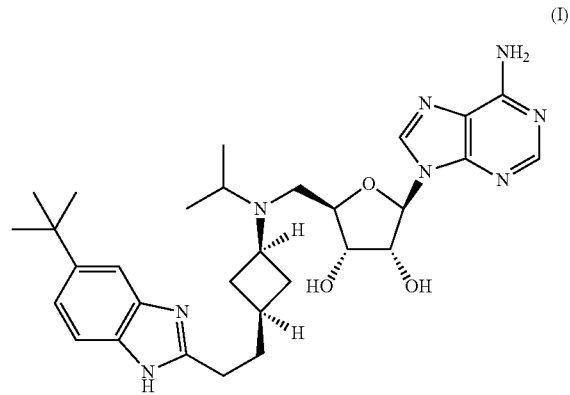 [SMILES: CC(C)N(C[C@H]1O[C@@H](n2cnc3c(N)ncnc32)[C@H](O)[C@@H]1O)[C@H]1C[C@@H](CCc2nc3cc(C(C)(C)C)ccc3[nH]2)C1]

(I)

or its N-oxide or a pharmaceutically acceptable salt thereof.

In certain embodiments, at least 20%, 30%, 40%, 50%, 60%, 70%, 80%, or 90% of the leukemic blast cells undergo maturation or differentiation.

In certain embodiments, in any method described herein, the compound of Formula (I) or its N-oxide or a pharmaceutically acceptable salt thereof can be administered at a dose of at least 36 mg/m$^2$/day, at least 45 mg/m$^2$/day, at least 54 mg/m$^2$/day, at least 70 mg/m$^2$/day, at least 80 mg/m$^2$/day, or at least 90 mg/m$^2$/day.

In certain embodiments, in any method described herein, the compound of Formula (I) or its N-oxide or a pharmaceutically acceptable salt thereof can be administered at an escalating dose. For example, the compound is administered, with or without a drug holiday, at a first dosage in a first cycle, and is then administered at a second dosage greater than the first dosage in a second cycle. Additional escalated doses that are greater than the second dosage can be administered. For example, the first dosage is at least about 36 mg/m$^2$/day, at least 45 mg/m$^2$/day, at least 54 mg/m$^2$/day, at least 70 mg/m$^2$/day, at least 80 mg/m$^2$/day, or at least 90 mg/m$^2$/day; and the second dosage is at least about at least 45 mg/m$^2$/day, at least 54 mg/m$^2$/day, at least 70 mg/m$^2$/day, at least 80 mg/m$^2$/day, at least 90 mg/m$^2$/day, or at least 100 mg/m$^2$/day. In one embodiment, the compound is administered, e.g., via IV infusion, for 21 days with a 7-day drug holiday in a 28-day cycle at a first dose of at least 45 mg/m$^2$/day (e.g., 45, 60, 70, or 80 mg/m$^2$/day), and is then administered, e.g., via IV infusion, for 21 days with a 7-day drug holiday in another 28-day cycle at a second dose of at least 60 mg/m$^2$/day (e.g., 60, 70, 80, 90, or 100 mg/m$^2$/day). In another embodiment, the compound is administered continuously, e.g., via IV infusion, for 28 days in a 28-day cycle at a first dose of at least 45 mg/m$^2$/day (e.g., 45, 60, 70, or 80 mg/m$^2$/day), and is then administered, e.g., via IV infusion, for 28 days in another 28-day cycle at a second dose of at least 60 mg/m$^2$/day (e.g., 60, 70, 80, 90, or 100 mg/m$^2$/day).

In certain embodiments, in any method described herein, the subject is an adult patient aged 18 years or older.

In certain embodiments, in any method described herein, the subject is a pediatric patient aged 12 months or younger (e.g., between 3 and 12 months old).

In certain embodiments, in any method described herein, the subject is a non-adult patient between 12 months and 18 years of age.

In certain embodiments, in any method described herein, the administration of the compound of Formula (I) or its N-oxide or a pharmaceutically acceptable salt thereof results in maturation or differentiation of leukemic blast cells and at least 20%, 50% or 80% of leukemic blast cells have undergone maturation or differentiation.

In certain embodiments, in any method described herein, at least 20%, 30%, 40%, 50%, 60%, 70%, 80%, or 90% of the leukemic blast cells undergo cell death or apoptosis.

In certain embodiments, in any method described herein, the subject can be a pediatric patient aged 3 months to 18 years.

In one aspect of the invention the MLL gene rearrangement is an 11q23 translocation or a partial tandem duplication of the MLL gene. Another aspect of the present invention is based in part upon the discovery that DOT1L inhibitors can effectively treat leukemia that is characterized by overexpression of HOXA9, FLT3, MEIS1 and/or DOT1L. Specifically, tumors or tumor cells having increased mRNA or protein level of at least one protein selected from the group consisting of HOXA9, FLT3, MEIS1 and DOT1L are sensitive to the DOT1L inhibitors of the present invention. Accordingly, the present invention provides methods of treating or alleviating a symptom of leukemia in a subject by administering a therapeutically effective amount of a DOT1L inhibitor (e.g., an effective amount of Formula (I) or its N-oxide or a pharmaceutically acceptable salt thereof).

The compounds of the present invention inhibit the histone methyltransferase activity of DOT1L or a mutant thereof. Based upon the surprising discovery that methylation regulation by DOT1L involves in tumor formation, particular tumors bearing an increased mRNA, protein and/or activity (function) level of at least one protein selected from the group consisting of HOXA9, FLT3, MEIS1 and DOT1L, the compounds described herein are suitable candidates for treating cancers, i.e., to decrease methylation or restore methylation to roughly its level in counterpart normal cells.

The present invention features a method for treating or alleviating a symptom of cancer. The method includes administering to a subject in need thereof, a therapeutically effective amount of a compound of the present invention, or a pharmaceutically acceptable salt, prodrug, metabolite, polymorph, solvate, or stereoisomeror thereof.

The present invention provides methods for the treatment of a cancer mediated by DOT1 (e.g., DOT1L)-mediated protein methylation in a subject in need thereof by administering to a subject in need of such treatment, a therapeutically effective amount of a compound of the present invention, or a pharmaceutically acceptable salt, prodrug, metabolite, polymorph or solvate thereof. The present invention further provides the use of a compound of the present invention, or a pharmaceutically acceptable salt, prodrug, metabolite, polymorph or solvate thereof, for the preparation of a medicament useful for the treatment of a cancer mediated by DOT1L-mediated protein methylation.

The present invention provides methods for the treatment of a cancer the course of which is influenced by modulating the methylation status of histones or other proteins, wherein said methylation status is mediated at least in part by the activity of DOT1L. Modulation of the methylation status of histones can in turn influence the level of expression of target genes activated by methylation, and/or target genes suppressed by methylation. The method includes administering to a subject in need of such treatment, a therapeutically effective amount of a compound of the present invention, or a pharmaceutically acceptable salt, prodrug, metabolite, polymorph, solvate, or stereoisomeror thereof.

The present invention also provides methods of protecting against or preventing a cancer in which DOT1L-mediated protein methylation plays a part in a subject in need thereof by administering a therapeutically effective amount of compound of the present invention, or a pharmaceutically acceptable salt, prodrug, metabolite, polymorph or solvate thereof, to a subject in need of such treatment. The present invention also provides the use of compound of the present invention, or a pharmaceutically acceptable salt, prodrug, metabolite, polymorph, solvate, or stereoisomeror thereof, for the preparation of a medicament useful for the prevention of a cell proliferative disorder.

In one aspect, the cancer is a hematological cancer. For example, the hematological cancer is leukemia. In any method described herein, the leukemia is chronic myelomonocytic leukemia (CMML), acute myeloid leukemia (AML), acute lymphoid leukemia (ALL), acute mixed lineage leukemia, myelodysplastic syndrome, myeloproliferative neoplasia (MPN) or leukemia characterized by MLL gene rearrangement (e.g., MLL-r or partial tandem duplication of MLL (MLL-PTD)).

The present invention further provides the use of a compound of the present invention, or a pharmaceutically acceptable salt, ester, prodrug, metabolite, polymorph or solvate thereof in the treatment of leukemia, or, for the preparation of a medicament useful for the treatment of such leukemia. The leukemia can be acute or chronic leukemia. Preferably, the leukemia is acute myeloid leukemia, acute lymphocytic leukemia or mixed lineage leukemia. Exemplary leukemia that may be treated is mixed linage leukemia or leukemia characterized by MLL gene rearrangement (MLL-r). Preferably, the MLL-r that can be treated by the compound of the present invention is chimeric fusion of MLL, partial tandem duplication of the MLL gene (MLL-PTD) or non-rearranged MLL.

Mixed lineage leukemia is a genetically distinct form of acute leukemia that constitutes over 70% of infant leukemias and approximately 10% of adult acute myeloid leukemias (AML) (Hess, J. L. (2004), Trends Mol Med 10, 500-507; Krivtsov, A. V., and Armstrong, S. A. (2007), Nat Rev Cancer 7, 823-833). MLL-r leukemia represents a particularly aggressive form of leukemia and patients with this disease generally have poor prognoses; these patients often suffer from early relapse after treatment with current chemotherapies. There is thus a great and present need for new treatment modalities for patients suffering with MLL.

A universal hallmark of MLL-r disease is a chromosomal translocation affecting the MLL gene on chromosome 11q23 (Hess, 2004; Krivtsov and Armstrong, 2007). Normally, the MLL gene encodes for a SET-domain histone methyltransferase that catalyzes the methylation of lysine 4 of histone H3 (H3K4) at specific gene loci (Milne et al. (2002) Mol Cell 10, 1107-1117; Nakamura et al. (2002), Mol Cell 10, 1119-1128). Gene localization is conferred by specific interactions with recognition elements within MLL, external to the SET-domain (Ayton et al. (2004) Mol Cell Biol 24, 10470-10478; Slany et al., (1998) Mol Cell Biol 18, 122-129; Zeleznik-Le et al. (1994) Proc Natl Acad Sci USA 91, 10610-10614). In the disease-linked translocations, the catalytic SET-domain is lost and the remaining MLL protein is fused to a variety of partners, including members of the AF and ENL family of proteins such as AF4, AF9, AF10 and ENL (Hess, 2004; Krivtsov and Armstrong, 2007; Slany (2009) Haematologica 94, 984-993). These fusion partners are capable of interacting directly, or indirectly, with another histone methyltransferase, DOT1L (Bitoun et al. (2007) Hum Mol Genet 16, 92-106; Mohan et al. (2010) Genes Dev. 24, 574-589; Mueller et al. (2007) Blood 110, 4445-4454; Mueller et al. (2009) PLoS Biol 7, e1000249; Okada et al. (2005) Cell 121, 167-178; Park et al. (2010) Protein J 29, 213-223; Yokoyama et al. (2010) Cancer Cell 17, 198-212; Zhang et al. (2006) J Biol Chem 281, 18059-18068). As a result, translocation products retain gene-specific recognition elements within the remainder of the MLL protein, but also gain the ability to recruit DOT1L, to these locations (Monroe et al. (2010) Exp Hematol. 2010 Sep. 18. [Epub ahead of print] Pubmed PMID: 20854876; Mueller et al., 2007; Mueller et al., 2009; Okada et al., 2005). DOT1L catalyzes the methylation of H3K79, a chromatin modification associated with actively transcribed genes (Feng et al. (2002) Curr Biol 12, 1052-1058; Steger et al. (2008) Mol Cell Biol 28, 2825-2839). The ectopic H3K79 methylation that results from MLL fusion protein recruitment of DOT1L leads to enhanced expression of leukemogenic genes, including HOXA9 and MEIS1 (Guenther et al. (2008) Genes & Development 22, 3403-3408; Krivtsov et al. (2008) Nat Rev Cancer 7, 823-833; Milne et al. (2005) Cancer Res 65, 11367-11374; Monroe et al., 2010; Mueller et al., 2009; Okada et al., 2005; Thiel et al. (2010) Cancer Cell 17, 148-159). Hence, while DOT1L is not genetically altered in the disease per se, its mislocated enzymatic activity is a direct consequence of the chromosomal translocation affecting MLL patients; thus, DOT1L has been proposed to be a catalytic driver of leukemogenesis in this disease (Krivtsov et al., 2008; Monroe et al., 2010; Okada et al., 2005; Yokoyama et al. (2010) Cancer Cell 17, 198-212). Further support for a pathogenic role of DOT1L in MLL comes from studies in model systems that demonstrate a requirement for DOT1L in propagating the transforming activity of MLL fusion proteins (Mueller et al., 2007; Okada et al., 2005).

Evidence indicates that the enzymatic activity of DOT1L is critical to pathogenesis in MLL and inhibition of DOT1L may provide a pharmacologic basis for therapeutic intervention in this disease. Compound treatment results in selective, concentration-dependent killing of leukemia cells bearing the MLL-translocation without effect on non-MLL transformed cells. Gene expression analysis of inhibitor treated cells shows downregulation of genes aberrantly over expressed in MLL-rearranged leukemias and similarities with gene expression changes caused by genetic knockout of the DOT1L gene in a mouse model of MLL-AF9 leukemia.

MLL can be characterized by the genetic lesions of the MLL gene. Such genetic lesions include chromosomal rearrangements, such as translocations, deletions, and/or duplications of the MLL gene. MLL has been categorized or characterized as having a chimeric fusion of MLL, partial tandem duplication of the MLL gene (MLL-PTD), or non-rearranged MLL. Chromosomal rearrangements or translocations can be identified by methods known in the art. For example, chromosomal rearrangements resulting in chimeric fusions can be detected by probe-based assays, such as FISH (fluorescence in situ hybridization) or sequence amplification by PCR. Those chromosomal rearrangements that result in partial tandem duplications are often difficult to detect by probe-based assays, and therefore, other DNA sequencing methods known in the art may be used, such as Sanger sequencing, de novo sequencing, shotgun sequencing, or next generation sequencing methods. MLL-PTD can be identified by DNA sequencing. MLL chimeric fusions can be identified by FISH. Diagnosis of MLL can be performed by detection of rearrangements of the MLL gene, or increased mRNA, protein, and/or activity level of at least one protein selected from the group consisting of HOXA9, FLT3, MEIS1 and DOT1L, as further described herein.

Compounds of the present invention can selectively inhibit proliferation of tumor or tumor cells characterized with an increased mRNA, protein and/or activity (function) level of at least one protein selected from the group consisting of HOXA9, FLT3, MEIS1 and DOT1L.

The present invention also provides methods for treating or alleviating a symptom of leukemia characterized by the presence of a genetic lesion of MLL. For example, this method comprises obtaining sample from the subject; detecting the presence of a genetic lesion of MLL in the sample; and when the genetic lesion is present in the sample, administering to the subject a therapeutically effective amount of a DOT1L inhibitor (e.g., a compound of Formula (I)). The genetic lesion may be chimeric fusion of MLL or MLL-PTD.

The present invention also provides methods for treating a disorder medicated by translocation, deletion and/or duplication of a gene on chromosome 11q23, comprising administering to a subject in need thereof a therapeutically effective amount of a compound of Formula (I).

In other aspects, the present invention provides personalized medicine, treatment and/or cancer management for a subject by genetic screening of increased gene expression (mRNA or protein), and/or increased function or activity level of at least one protein selected from the group consisting of HOXA9, FLT3, MEIS1 and DOT1L in the subject. For example, the present invention provides methods for treating, preventing or alleviating a symptom of cancer or a precancerous condition by determining responsiveness of the subject to a DOT1L inhibitor and when the subject is responsive to the DOT1L inhibitor, administering to the subject a therapeutically effective amount of the DOT1L inhibitor, or a pharmaceutically acceptable salt, prodrug, metabolite, polymorph, solvate, or stereoisomeror thereof. The responsiveness is determined by obtaining a sample from the subject and detecting increased mRNA or protein, and/or increased activity level of at least one protein selected from the group consisting of HOXA9, FLT3, MEIS1 and DOT1L, and the presence of such gain of expression and/or function indicates that the subject is responsive to the DOT1L inhibitor. Once the responsiveness of a subject is determined, a therapeutically effective amount of a DOT1L inhibitor, for example, any compound of the invention can be administered. The therapeutically effective amount of a DOT1L inhibitor can be determined by one of ordinary skill in the art.

As used herein, the term "responsiveness" is interchangeable with terms "responsive", "sensitive", and "sensitivity", and it is meant that a subject is showing therapeutic responses when administered a DOT1L inhibitor, e.g., leukemic blast cells undergo maturation or differentiation or cell death or apoptosis or reduction in number or volume. This term is also meant that a subject will or has a higher probability, relative to the population at large, of showing therapeutic responses when administered a DOT1L inhibitor, e.g., tumor cells or tumor tissues of the subject undergo apoptosis and/or necrosis, and/or display maturation or differentiation.

As used herein, a "subject" is interchangeable with a "subject in need thereof", both of which refers to a subject having a disorder in which DOT1L-mediated protein methylation plays a part, or a subject having an increased risk of developing such disorder relative to the population at large. A subject in need thereof may be a subject having a disorder associated DOT1L. A subject in need thereof can have a precancerous condition. Preferably, a subject in need thereof has cancer. A subject in need thereof can have cancer associated with DOT1L. A subject in need thereof can have cancer associated with increased expression (mRNA or protein) and/or activity level of at least one protein selected from the group consisting of HOXA9, FLT3, MEIS1 and DOT1L. In a preferred aspect, a subject in need thereof has a hematologic cancer, wherein the hematologic cancer is leukemia or lymphoma. Exemplary leukemia is MLL-r leukemia. Other hematologic cancers of the present invention can include multiple myeloma, lymphoma (including Hodgkin's lymphoma, non-Hodgkin's lymphoma, childhood lymphomas, and lymphomas of lymphocytic and cutaneous origin), leukemia (including childhood leukemia, hairy-cell leukemia, acute lymphocytic leukemia, acute myelocytic leukemia, chronic lymphocytic leukemia, chronic myelocytic leukemia, chronic myelogenous leukemia, and mast cell leukemia), myeloid neoplasms and mast cell neoplasms.

As used herein, a "subject" includes a mammal. The mammal can be e.g., a human or appropriate non-human mammal, such as primate, mouse, rat, dog, cat, cow, horse, goat, camel, sheep or a pig. The subject can also be a bird or fowl. In one embodiment, the mammal is a human. A subject can be male or female. In one aspect of the invention that subject is a pediatric (non-adult) patient aged 3 months to 18 years. In one embodiment, the subject is a pediatric patient aged 12 months or younger.

A subject in need thereof can be one who has been previously diagnosed or identified as having cancer or a precancerous condition. A subject in need thereof can also be one who is having (suffering from) cancer or a precancerous condition. Alternatively, a subject in need thereof can be one who is having an increased risk of developing such disorder relative to the population at large (i.e., a subject who is predisposed to developing such disorder relative to the population at large).

Optionally a subject in need thereof has already undergone, is undergoing or will undergo, at least one therapeutic intervention for the cancer or precancerous condition.

A subject in need thereof may have refractory cancer on most recent therapy. "Refractory cancer" means cancer that does not respond to treatment. The cancer may be resistant at the beginning of treatment or it may become resistant during treatment. Refractory cancer is also called resistant cancer. In some embodiments, the subject in need thereof has cancer recurrence following remission on most recent therapy. In some embodiments, the subject in need thereof received and failed all known effective therapies for cancer treatment. In some embodiments, the subject in need thereof received at least one prior therapy.

In some embodiments, a subject in need thereof may have a secondary cancer as a result of a previous therapy. "Secondary cancer" means cancer that arises due to or as a result from previous carcinogenic therapies, such as chemotherapy. In some embodiments, the secondary cancer is a hematologic cancer, such as leukemia.

In any method of the present invention, a subject in need thereof may have increased mRNA, protein, and/or activity level of at least of at least one signaling component downstream of at least one protein selected from the group consisting of HOXA9, FLT3, MEIS1 and DOT1L. Such downstream components are readily known in the art, and can include other transcription factors, or signaling proteins.

Accordingly, an increase in mRNA or protein expression and/or activity levels can be detected using any suitable method available in the art. For example, an increase in activity level can be detected by measuring the biological function of a gene product, such as the histone methyltransferase activity of DOT1L (i.e., methylation of histone substrates such as H3K79 by immunoblot); transcriptional activity of HOXA9 or MEIS1 (i.e., expression levels of HOXA9 or MEIS1 target genes by RT-PCR); or phosphorylation activity of FLT3 (i.e., phosphorylation status of FLT3 targets by immunoblot or radioimmunoassay). Alternatively, a gain of function mutation can be determined by detecting any alternation in a nucleic acid sequence encoding a protein selected from the group consisting of HOXA9, FLT3, MEIS1 and DOT1L. For example, a nucleic acid sequence encoding HOXA9, FLT3, MEIS1 and DOT1L having a gain of function mutation can be detected by whole-genome resequencing or target region resequencing (the latter also known as targeted resequencing) using suitably selected sources of DNA and polymerase chain reaction (PCR) primers in accordance with methods well known in the art. The method typically and generally entails the steps of genomic DNA purification, PCR amplification to amplify the region of interest, cycle sequencing, sequencing reaction cleanup, capillary electrophoresis, and/or data analysis. Alternatively or in addition, the method may include the use of microarray-based targeted region genomic DNA capture and/or sequencing. Kits, reagents, and methods for selecting appropriate PCR primers and performing resequencing are commercially available, for example, from Applied Biosystems, Agilent, and NimbleGen (Roche Diagnostics GmbH). Detection of mRNA expression can be detected by methods known in the art, such as Northern blot, nucleic acid PCR, and quantitative RT-PCR. Detection of polypeptide expression (i.e., wild-type or mutant) can be carried out with any suitable immunoassay in the art, such as Western blot analysis.

By "sample" it means any biological sample derived from the subject, includes but is not limited to, cells, tissues samples, body fluids (including, but not limited to, mucus, blood, plasma, serum, urine, saliva, and semen), tumor cells, and tumor tissues. Preferably, the sample is selected from bone marrow, peripheral blood cells, blood, plasma and serum. Samples can be provided by the subject under treatment or testing. Alternatively samples can be obtained by the physician according to routine practice in the art in accordance with the NCCN AML guidelines (Appendix 2 of U.S. Provisional Application Ser. No. 61/903,912 filed Nov. 13, 2013, the content of which is incorporated herein by reference in its entirety).

The present invention also provides methods for diagnosing leukemia in a subject by obtaining a sample from the subject and detecting an increased mRNA, protein and/or activity level of at least one protein selected from the group consisting of HOXA9, FLT3, MEIS1 and DOT1L, and the presence of such increased mRNA, protein and/or activity level indicates that the subject has or is at risk for developing leukemia compared to a subject without such increased mRNA, protein and/or activity level, or a subject that does not have leukemia.

Any compound (e.g., a DOT1L inhibitor) of the present invention can be used for the methods described above. In one embodiment, the DOT1L inhibitor used in any preceding methods is Compound of Formula (I) (or Compound A2 or EPZ-5676) having the formula:

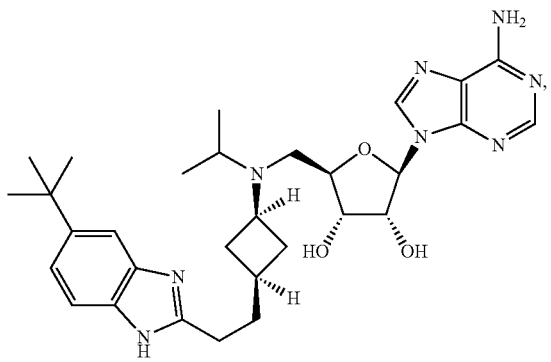 [SMILES: CC(C)N(C[C@H]1O[C@@H](n2cnc3c(N)ncnc32)[C@H](O)[C@@H]1O)[C@H]1C[C@@H](CCc2nc3cc(C(C)(C)C)ccc3[nH]2)C1]

or a pharmaceutically acceptable salt, prodrug, metabolite, polymorph, solvate, or stereoisomer thereof, or EPZ-4777 having the following formula:

(EPZ-4777)

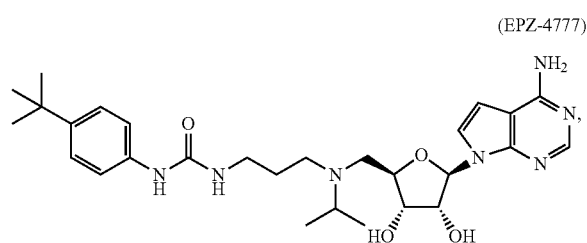 [SMILES: CC(C)N(CCCNC(=O)Nc1ccc(C(C)(C)C)cc1)C[C@H]1O[C@@H](n2ccc3c(N)ncnc32)[C@H](O)[C@@H]1O]

or a pharmaceutically acceptable salt, prodrug, metabolite, polymorph, solvate, or stereoisomer thereof. However, it should be appreciated that other DOT1L inhibitors as described herein can be used.

A "cell proliferative disorder of the hematologic system" is a cell proliferative disorder involving cells of the hematologic system. A cell proliferative disorder of the hematologic system can include lymphoma, leukemia, myeloid neoplasms, mast cell neoplasms, myelodysplasia, benign monoclonal gammopathy, lymphomatoid granulomatosis, lymphomatoid papulosis, polycythemia vera, chronic myelocytic leukemia, agnogenic myeloid metaplasia, and essential thrombocythemia. A cell proliferative disorder of the hematologic system can include hyperplasia, dysplasia, and metaplasia of cells of the hematologic system. Preferably, compositions of the present invention may be used to treat a cancer selected from the group consisting of a hematologic cancer of the present invention or a hematologic cell proliferative disorder of the present invention. A hematologic cancer of the present invention can include multiple myeloma, lymphoma (including Hodgkin's lymphoma, non-Hodgkin's lymphoma, childhood lymphomas, and lymphomas of lymphocytic and cutaneous origin), leukemia (including childhood leukemia, hairy-cell leukemia, acute lymphocytic leukemia, acute myelocytic leukemia, chronic lymphocytic leukemia, chronic myelocytic leukemia, chronic myelogenous leukemia, and mast cell leukemia), myeloid neoplasms and mast cell neoplasms.

A cancer that is to be treated can include a tumor that has been determined to be less than or equal to about 2 centimeters in diameter. A cancer that is to be treated can include a tumor that has been determined to be from about 2 to about 5 centimeters in diameter. A cancer that is to be treated can include a tumor that has been determined to be greater than or equal to about 3 centimeters in diameter. A cancer that is to be treated can include a tumor that has been determined to be greater than 5 centimeters in diameter. A cancer that is to be treated can be classified by microscopic appearance as well differentiated, moderately differentiated, poorly differentiated, or undifferentiated. A cancer that is to be treated can be classified by microscopic appearance with respect to mitosis count (e.g., amount of cell division) or nuclear pleiomorphism (e.g., change in cells). A cancer that is to be treated can be classified by microscopic appearance as being associated with areas of necrosis (e.g., areas of dying or degenerating cells). A cancer that is to be treated can be classified as having an abnormal karyotype, having an abnormal number of chromosomes, or having one or more chromosomes that are abnormal in appearance. A cancer that is to be treated can be classified as being aneuploid, triploid, tetraploid, or as having an altered ploidy. A cancer that is to be treated can be classified as having a chromosomal translocation, or a deletion or duplication of an entire chromosome, or a region of deletion, duplication or amplification of a portion of a chromosome.

A cancer that is to be treated can be evaluated by DNA cytometry, flow cytometry, or image cytometry. A cancer that is to be treated can be typed as having 10%, 20%, 30%, 40%, 50%, 60%, 70%, 80%, or 90% of cells in the synthesis stage of cell division (e.g., in S phase of cell division). A cancer that is to be treated can be typed as having a low S-phase fraction or a high S-phase fraction.

As used herein, a "normal cell" is a cell that cannot be classified as part of a "cell proliferative disorder". A normal cell lacks unregulated or abnormal growth, or both, that can lead to the development of an unwanted condition or disease. Preferably, a normal cell possesses normally functioning cell cycle checkpoint control mechanisms.

As used herein, "contacting a cell" refers to a condition in which a compound or other composition of matter is in direct contact with a cell, or is close enough to induce a desired biological effect in a cell.

As used herein, "candidate compound" refers to a compound of the present invention, or a pharmaceutically acceptable salt, prodrug, metabolite, polymorph or solvate thereof, that has been or will be tested in one or more in vitro or in vivo biological assays, in order to determine if that compound is likely to elicit a desired biological or medical response in a cell, tissue, system, animal or human that is being sought by a researcher or clinician. A candidate compound is a compound of the present invention, or a pharmaceutically acceptable salt, prodrug, metabolite, polymorph or solvate thereof. The biological or medical response can be the treatment of cancer. The biological or medical response can be treatment or prevention of a cell proliferative disorder. In vitro or in vivo biological assays can include, but are not limited to, enzymatic activity assays, electrophoretic mobility shift assays, reporter gene assays, in vitro cell viability assays, and the assays described herein.

For example, an in vitro biological assay that can be used includes the steps of (1) mixing a histone substrate (e.g., an isolated histone sample for a histone or modified histone of interest, or an isolated oligonucleosome substrate) with recombinant DOT1L enzyme (e.g., recombinant protein containing amino acids 1-416); (2) adding a candidate compound of the invention to this mixture; (3) adding non-radioactive and $^3$H-labeled S-Adenosyl methionine (SAM) to start the reaction; (4) adding excessive amount of non-radioactive SAM to stop the reaction; (4) washing off the free non-incorporated $^3$H-SAM; and (5) detecting the quantity of $^3$H-labeled histone substrate by any methods known in the art (e.g., by a PerkinElmer TopCount platereader).

For example, an in vitro cell viability assay that can be used includes the steps of (1) culturing cells (e.g., EOL-1 cells) in the presence of increasing concentration of candidate compound (e.g., Compound A2); (2) determining viable cell number every 3-4 days by methods known in the art (e.g., using the Millipore Guava Viacount assay); (3) plotting concentration-dependence growth curves; and optionally (4) calculating $IC_{50}$ values from the concentration-dependence growth curves using methods known in the art (e.g., using GraphPad Prism Software).

For example, a histone methylation assay that can be used includes the steps of (1) culturing cells (e.g., EOL-1 cells) in the presence of candidate compound (e.g., Compound A2); (2) harvesting the cells; (3) extracting histone proteins, using methods known in the art (e.g., sulfuric acid precipitation); (4) fractionating histone extracts by SDS-PAGE electrophoresis and transferring to a filter; (5) probing the filter with antibodies specific to a protein or methylated-protein of interest (e.g., H3K79me2-specific antibody and total histone H3-specific antibody); and (6) detecting the signal of the antibodies using methods known in the art (e.g., Li-cor Odyssey infrared imager).

For example, a gene expression assay that can be used includes the steps of (1) culturing cells (e.g., EOL-1, Molm13, MV411, LOUCY, SemK2, Reh, HL60, BV173, or Jurkat cells) in the presence or absence of candidate compound (e.g., Compound A2); (2) harvesting the cells; (3) extracting the RNA using methods known in the art (e.g., Qiagen RNeasy Kit); (4) synthesizing cDNA from the extracted RNA (e.g., Applied Biosystems reverse transcriptase kit); (5) preparing qPCR reactions using, for example, primers and probes (e.g., predesigned labeled primer and probe sets for HOXA9, MEIS1, FLT3, DOT1L, and β2-microgobulin from Applied Biosystems), synthesized sample cDNA, and qPCR master mix reagent (e.g., Applied Biosystems Taqman universal PCR master mix); (6)

running samples on PCR machine (e.g., Applied Biosystems); (7) analysis of the data and calculation of relative gene expression.

As used herein, "monotherapy" refers to the administration of a single active or therapeutic compound to a subject in need thereof. Preferably, monotherapy will involve administration of a therapeutically effective amount of a single active compound. For example, cancer monotherapy with one of the compound of the present invention, or a pharmaceutically acceptable salt, prodrug, metabolite, analog or derivative thereof, to a subject in need of treatment of cancer. In one aspect, the single active compound is a compound of the present invention, or a pharmaceutically acceptable salt, prodrug, metabolite, polymorph or solvate thereof.

As used herein, "treating" or "treat" describes the management and care of a patient for the purpose of combating a disease, condition, or disorder and includes the administration of a compound of the present invention, or a pharmaceutically acceptable salt, prodrug, metabolite, polymorph or solvate thereof, to alleviate the symptoms or complications of a disease, condition or disorder, or to eliminate the disease, condition or disorder.

A compound of the present invention, or a pharmaceutically acceptable salt, prodrug, metabolite, polymorph or solvate thereof, can also be used to prevent a disease, condition or disorder. As used herein, "preventing" or "prevent" describes reducing or eliminating the onset of the symptoms or complications of the disease, condition or disorder.

As used herein, the term "alleviate" is meant to describe a process by which the severity of a sign or symptom of a disorder is decreased. Importantly, a sign or symptom can be alleviated without being eliminated. In a preferred embodiment, the administration of pharmaceutical compositions of the invention leads to the elimination of a sign or symptom, however, elimination is not required. In one aspect of the invention the symptom of leukemia is fever, cachexia, or leukemia cutis. Effective dosages are expected to decrease the severity of a sign or symptom. For instance, a sign or symptom of a disorder such as cancer, which can occur in multiple locations, is alleviated if the severity of the cancer is decreased within at least one of multiple locations.

As used herein, the term "severity" is meant to describe the potential of cancer to transform from a precancerous, or benign, state into a malignant state. Alternatively, or in addition, severity is meant to describe a cancer stage, for example, according to the TNM system (accepted by the International Union Against Cancer (UICC) and the American Joint Committee on Cancer (AJCC)) or by other art-recognized methods. Cancer stage refers to the extent or severity of the cancer, based on factors such as the location of the primary tumor, tumor size, number of tumors, and lymph node involvement (spread of cancer into lymph nodes).

As used herein the term "symptom" is defined as an indication of disease, illness, injury, or that something is not right in the body. Symptoms are felt or noticed by the individual experiencing the symptom, but may not easily be noticed by others. Others are defined as non-health-care professionals.

As used herein the term "sign" is also defined as an indication that something is not right in the body. But signs are defined as things that can be seen by a doctor, nurse, or other health care professional.

Cancer is a group of diseases that may cause almost any sign or symptom. The signs and symptoms will depend on where the cancer is, the size of the cancer, and how much it affects the nearby organs or structures. If a cancer spreads (metastasizes), then symptoms may appear in different parts of the body.

Treating cancer can result in an increase in average survival time of a population of treated subjects in comparison to a population receiving carrier alone. Preferably, the average survival time is increased by more than 30 days; more preferably, by more than 60 days; more preferably, by more than 90 days; and most preferably, by more than 120 days. An increase in average survival time of a population may be measured by any reproducible means. An increase in average survival time of a population may be measured, for example, by calculating for a population the average length of survival following initiation of treatment with an active compound. An increase in average survival time of a population may also be measured, for example, by calculating for a population the average length of survival following completion of a first round of treatment with an active compound.

Treating cancer can result in an increase in average survival time of a population of treated subjects in comparison to a population of untreated subjects. Preferably, the average survival time is increased by more than 30 days; more preferably, by more than 60 days; more preferably, by more than 90 days; and most preferably, by more than 120 days. An increase in average survival time of a population may be measured by any reproducible means. An increase in average survival time of a population may be measured, for example, by calculating for a population the average length of survival following initiation of treatment with an active compound. An increase in average survival time of a population may also be measured, for example, by calculating for a population the average length of survival following completion of a first round of treatment with an active compound.

Treating cancer can result in increase in average survival time of a population of treated subjects in comparison to a population receiving monotherapy with a drug that is not a compound of the present invention, or a pharmaceutically acceptable salt, prodrug, metabolite, analog or derivative thereof. Preferably, the average survival time is increased by more than 30 days; more preferably, by more than 60 days; more preferably, by more than 90 days; and most preferably, by more than 120 days. An increase in average survival time of a population may be measured by any reproducible means. An increase in average survival time of a population may be measured, for example, by calculating for a population the average length of survival following initiation of treatment with an active compound. An increase in average survival time of a population may also be measured, for example, by calculating for a population the average length of survival following completion of a first round of treatment with an active compound.

Treating cancer can result in a decrease in the mortality rate of a population of treated subjects in comparison to a population receiving carrier alone. Treating cancer can result in a decrease in the mortality rate of a population of treated subjects in comparison to an untreated population. Treating cancer can result in a decrease in the mortality rate of a population of treated subjects in comparison to a population receiving monotherapy with a drug that is not a compound of the present invention, or a pharmaceutically acceptable salt, prodrug, metabolite, analog or derivative thereof. Preferably, the mortality rate is decreased by more than 2%; more preferably, by more than 5%; more preferably, by more than 10%; and most preferably, by more than 25%. A decrease in the mortality rate of a population of treated subjects may be measured by any reproducible means. A decrease in the mortality rate of a population may be measured, for example, by calculating for a population the average number of disease-related deaths per unit time following initiation of treatment with an active compound. A decrease in the mortality rate of a population may also be measured, for example, by calculating for a population the average number of disease-related deaths per unit time following completion of a first round of treatment with an active compound.

A compound of the present invention, or a pharmaceutically acceptable salt, prodrug, metabolite, polymorph or solvate thereof, can modulate the activity of a molecular target (e.g., a target protein methyltransferase). Modulating refers to stimulating or inhibiting an activity of a molecular target. Preferably, a compound of the present invention, or a pharmaceutically acceptable salt, prodrug, metabolite, polymorph or solvate thereof, modulates the activity of a molecular target if it stimulates or inhibits the activity of the molecular target by at least 2-fold relative to the activity of the molecular target under the same conditions but lacking only the presence of said compound. More preferably, a compound of the present invention, or a pharmaceutically acceptable salt, prodrug, metabolite, polymorph or solvate thereof, modulates the activity of a molecular target if it stimulates or inhibits the activity of the molecular target by at least 5-fold, at least 10-fold, at least 20-fold, at least 50-fold, at least 100-fold relative to the activity of the molecular target under the same conditions but lacking only the presence of said compound. The activity of a molecular target may be measured by any reproducible means. The activity of a molecular target may be measured in vitro or in vivo. For example, the activity of a molecular target may be measured in vitro by an enzymatic activity assay or a DNA binding assay, or the activity of a molecular target may be measured in vivo by assaying for expression of a reporter gene.

A compound of the present invention, or a pharmaceutically acceptable salt, prodrug, metabolite, polymorph or solvate thereof, does not significantly modulate the activity of a molecular target if the addition of the compound does not stimulate or inhibit the activity of the molecular target by greater than 10% relative to the activity of the molecular target under the same conditions but lacking only the presence of said compound.

As used herein, the term "isozyme selective" means preferential inhibition or stimulation of a first isoform of an enzyme in comparison to a second isoform of an enzyme (e.g., preferential inhibition or stimulation of a protein methyltransferase isozyme alpha in comparison to a protein methyltransferase isozyme beta). Preferably, a compound of the present invention, or a pharmaceutically acceptable salt, prodrug, metabolite, polymorph or solvate thereof, demonstrates a minimum of a fourfold differential, preferably a tenfold differential, more preferably a fifty fold differential, in the dosage required to achieve a biological effect. Preferably, a compound of the present invention, or a pharmaceutically acceptable salt, prodrug, metabolite, polymorph or solvate thereof, demonstrates this differential across the range of inhibition, and the differential is exemplified at the $IC_{50}$, i.e., a 50% inhibition, for a molecular target of interest.

Administering a compound of the present invention, or a pharmaceutically acceptable salt, prodrug, metabolite, polymorph or solvate thereof, to a cell or a subject in need thereof can result in modulation (i.e., stimulation or inhibition) of an activity of a protein methyltransferase of interest.

The present invention provides methods to assess biological activity of a compound of the present invention, or a pharmaceutically acceptable salt, prodrug, metabolite, polymorph or solvate thereof or methods of identifying a test compound as a modulator (e.g., an inhibitor) of DOT1L. DOT1L polypeptides and nucleic acids can be used to screen for compounds that bind to and/or modulate (e.g., increase or decrease) one or more biological activities of DOT1L, including but not limited to H3K79 HMTase activity, SAM binding activity, histone and/or nucleosome binding activity, AF10 binding activity, AF10-MLL or other MLL fusion protein binding activity, and/or any other biological activity of interest. A DOT1L polypeptide can be a functional fragment of a full-length DOT1L polypeptide or functional equivalent thereof, and may comprise any DOT1 domain of interest, including but not limited to the catalytic domain, the SAM binding domain and/or the positively charged domain, the AF10 interaction domain and/or a nuclear export signal.

Methods of assessing DOT1L binding to histones, nucleosomes, nucleic acids or polypeptides can be carried out using standard techniques that will be apparent to those skilled in the art (see the Exemplification for exemplary methods). Such methods include yeast and mammalian two-hybrid assays and co-immunoprecipitation techniques.

For example, a compound that modulates DOT1L H3K79 HMTase activity can be verified by: contacting a DOT1L polypeptide with a histone or peptide substrate comprising H3 in the presence of a test compound; detecting the level of H3K79 methylation of the histone or peptide substrate under conditions sufficient to provide H3K79 methylation, wherein an elevation or reduction in H3K79 methylation in the presence of the test compound as compared with the level of histone H3K79 methylation in the absence of the test compound indicates that the test compound modulates DOT1L H3K79 HMTase activity.

The screening methods of the invention can be carried out in a cell-based or cell-free system. As a further alternative, the assay can be performed in a whole animal (including transgenic non-human animals). Further, with respect to cell-based systems, the DOT1L polypeptide (or any other polypeptide used in the assay) can be added directly to the cell or can be produced from a nucleic acid in the cell. The nucleic acid can be endogenous to the cell or can be foreign (e.g., a genetically modified cell).

In some assays, immunological reagents, e.g., antibodies and antigens, are employed. Fluorescence can be utilized in the measurement of enzymatic activity in some assays. As used herein, "fluorescence" refers to a process through which a molecule emits a photon as a result of absorbing an incoming photon of higher energy by the same molecule. Specific methods for assessing the biological activity of the disclosed compounds are described in the examples.

Administering a compound of the present invention, or a pharmaceutically acceptable salt, prodrug, metabolite, polymorph or solvate thereof, to a cell or a subject in need thereof results in modulation (i.e., stimulation or inhibition) of an activity of an intracellular target (e.g., substrate). Several intracellular targets can be modulated with the compounds of the present invention, including, but not limited to, protein methyltrasferase.

Activating refers to placing a composition of matter (e.g., protein or nucleic acid) in a state suitable for carrying out a desired biological function. A composition of matter capable of being activated also has an unactivated state. An activated composition of matter may have an inhibitory or stimulatory biological function, or both.

Elevation refers to an increase in a desired biological activity of a composition of matter (e.g., a protein or a nucleic acid). Elevation may occur through an increase in concentration of a composition of matter.

As used herein, "a cell cycle checkpoint pathway" refers to a biochemical pathway that is involved in modulation of a cell cycle checkpoint. A cell cycle checkpoint pathway may have stimulatory or inhibitory effects, or both, on one or more functions comprising a cell cycle checkpoint. A cell cycle checkpoint pathway is comprised of at least two compositions of matter, preferably proteins, both of which contribute to modulation of a cell cycle checkpoint. A cell cycle checkpoint pathway may be activated through an activation of one or more members of the cell cycle checkpoint pathway. Preferably, a cell cycle checkpoint pathway is a biochemical signaling pathway.

As used herein, "cell cycle checkpoint regulator" refers to a composition of matter that can function, at least in part, in modulation of a cell cycle checkpoint. A cell cycle checkpoint regulator may have stimulatory or inhibitory effects, or both, on one or more functions comprising a cell cycle checkpoint. A cell cycle checkpoint regulator can be a protein or not a protein.

Treating cancer or a cell proliferative disorder can result in cell death, and preferably, cell death results in a decrease of at least 10% in number of cells in a population. More preferably, cell death means a decrease of at least 20%; more preferably, a decrease of at least 30%; more preferably, a decrease of at least 40%; more preferably, a decrease of at least 50%; most preferably, a decrease of at least 75%. Number of cells in a population may be measured by any reproducible means. A number of cells in a population can be measured by fluorescence activated cell sorting (FACS), immunofluorescence microscopy and light microscopy. Methods of measuring cell death are as shown in Li et al., *Proc Natl Acad Sci USA*. 100(5): 2674-8, 2003. In an aspect, cell death occurs by apoptosis.

Preferably, an effective amount of a compound of the present invention, or a pharmaceutically acceptable salt, prodrug, metabolite, polymorph or solvate thereof, is not significantly cytotoxic to normal cells. A therapeutically effective amount of a compound is not significantly cytotoxic to normal cells if administration of the compound in a therapeutically effective amount does not induce cell death in greater than 10% of normal cells. A therapeutically effective amount of a compound does not significantly affect the viability of normal cells if administration of the compound in a therapeutically effective amount does not induce cell death in greater than 10% of normal cells. In an aspect, cell death occurs by apoptosis.

Contacting a cell with a compound of the present invention, or a pharmaceutically acceptable salt, prodrug, metabolite, polymorph or solvate thereof, can induce or activate cell death selectively in cancer cells. Administering to a subject in need thereof a compound of the present invention, or a pharmaceutically acceptable salt, prodrug, metabolite, polymorph or solvate thereof, can induce or activate cell death selectively in cancer cells. Contacting a cell with a compound of the present invention, or a pharmaceutically acceptable salt, prodrug, metabolite, polymorph or solvate thereof, can induce cell death selectively in one or more cells affected by a cell proliferative disorder. Preferably, administering to a subject in need thereof a compound of the present invention, or a pharmaceutically acceptable salt, prodrug, metabolite, polymorph or solvate thereof, induces cell death selectively in one or more cells affected by a cell proliferative disorder.

The present invention relates to a method of treating or preventing cancer by administering a compound of the present invention, or a pharmaceutically acceptable salt, prodrug, metabolite, polymorph or solvate thereof, to a subject in need thereof, where administration of the compound of the present invention, or a pharmaceutically acceptable salt, prodrug, metabolite, polymorph or solvate thereof, results in one or more of the following: accumulation of cells in G1 and/or S phase of the cell cycle, cytotoxicity via cell death in cancer cells without a significant amount of cell death in normal cells, antitumor activity in animals with a therapeutic index of at least 2, and activation of a cell cycle checkpoint. As used herein, "therapeutic index" is the maximum tolerated dose divided by the efficacious dose.

One skilled in the art may refer to general reference texts for detailed descriptions of known techniques discussed herein or equivalent techniques. These texts include Ausubel et al., *Current Protocols in Molecular Biology*, John Wiley and Sons, Inc. (2005); Sambrook et al., *Molecular Cloning, A Laboratory Manual* ($3^{rd}$ edition), Cold Spring Harbor Press, Cold Spring Harbor, N.Y. (2000); Coligan et al., *Current Protocols in Immunology*, John Wiley & Sons, N.Y.; Enna et al., *Current Protocols in Pharmacology*, John Wiley & Sons, N.Y.; Fingl et al., *The Pharmacological Basis of Therapeutics* (1975), Remington's Pharmaceutical Sciences, Mack Publishing Co., Easton, Pa., $18^{th}$ edition (1990). These texts can, of course, also be referred to in making or using an aspect of the invention Any other disease in which epigenetic methylation, which is mediated by DOT1, plays a role may be treatable or preventable using compounds and methods described herein.

As used herein, a DOT1L inhibitor is an inhibitor of DOT1L-mediated protein methylation (e.g., an inhibitor of histone methylation). In some embodiments, a DOT1L inhibitor is a small molecule inhibitor of DOT1L. In some embodiments, a DOT1L inhibitor is a compound of formula:

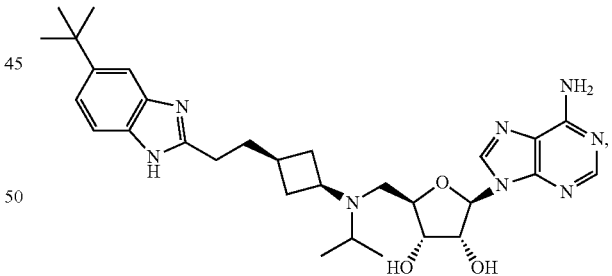

(EPZ-5676

(EPZ-5676, or (2R,3R,4S,5R)-2-(6-amino-9H-purin-9-yl)-5-((((1r,3S)-3-(2-(5-(tert-butyl)-1H-benzo[d]imidazol-2yl)ethyl)cyclobutyl)(isopropyl)amino)methyl)tetrahydrofuran-3,4-diol (563.4 $(M+H)^+$) or a pharmaceutically acceptable salt, prodrug, metabolite, polymorph, solvate, or stereoisomer thereof.

Other DOT1L inhibitors suitable for use according to methods described herein are provided in WO2012/075381, WO2012/075492, WO2012/082436, WO2012/75500, WO2014/026198, WO2014/035140, and US2014/0100184, the contents of each of which are hereby incorporated by reference in their entireties. The activity of a DOT1L inhibitor can be evaluated in an assay, for example by comparing the histone methyltransferase activity of DOT1L (e.g., methylation of histone substrates such as H3K79 by immunoblot) in the presence or absence of various amounts of the inhibitor.

The invention also relates to a pharmaceutical composition of a therapeutically effective amount of a compound of any of the Formulae disclosed herein and a pharmaceutically acceptable carrier.

The invention also relates to a pharmaceutical composition of a therapeutically effective amount of a salt of a compound of any of the Formulae disclosed herein and a pharmaceutically acceptable carrier.

The invention also relates to a pharmaceutical composition of a therapeutically effective amount of a hydrate of a compound of any of the Formulae disclosed herein and a pharmaceutically acceptable carrier.

The present invention provides methods of treating or preventing cancer. The present invention provides methods of treating cancer. The present invention also provides methods of preventing cancer. The method includes administering to a subject in need thereof a therapeutically effective amount of the compound of any of the Formulae disclosed herein. The cancer can be a hematological cancer. Preferably, the cancer is leukemia. More preferably, the cancer is acute myeloid leukemia, acute lymphocytic leukemia or mixed lineage leukemia.

The present invention provides methods of treating or preventing a disease or disorder mediated by translocation of a gene on chromosome 11 q23. The present invention provides methods of treating a disease or disorder mediated by translocation of a gene on chromosome 11q23. The present invention also provides methods of preventing a disease or disorder mediated by translocation of a gene on chromosome 11 q23. The method includes administering to a subject in need thereof a therapeutically effective amount of the compound of any of the Formulae disclosed herein.

The present invention provides methods of treating or preventing a disease or disorder in which DOT1L-mediated protein methylation plays a part or a disease or disorder mediated by DOT1L-mediated protein methylation. The present invention provides methods of treating a disease or disorder in which DOT1L-mediated protein methylation plays a part or a disease or disorder mediated by DOT1L-mediated protein methylation. The present invention also provides methods of preventing a disease or disorder in which DOT1L-mediated protein methylation plays a part or a disease or disorder mediated by DOT1L-mediated protein methylation. The method includes administering to a subject in need thereof a therapeutically effective amount of the compound of any of the Formulae disclosed herein.

The present invention provides methods of inhibiting DOT1L activity in a cell. The method includes contacting the cell with an effective amount of one or more of the compound of any of the Formulae disclosed herein.

Still another aspect of the invention relates to a method of reducing the level of Histone H3 Lysine residue 79 (H3-K79) methylation in a cell. The method includes contacting a cell with a compound of the present invention. Such method can be used to ameliorate any condition which is caused by or potentiated by the activity of DOT1L through H3-K79 methylation.

The present invention relates to use of the compounds disclosed herein in preparation of a medicament for treating or preventing cancer. The use includes a compound of any of the Formulae disclosed herein for administration to a subject in need thereof in a therapeutically effective amount. The cancer can be a hematological cancer. Preferably, the cancer is leukemia. More preferably, the cancer is acute myeloid leukemia, acute lymphocytic leukemia or mixed lineage leukemia.

The present invention provides use of the compounds disclosed herein in preparation of a medicament for treating or preventing a disease or disorder mediated by translocation of a gene on chromosome 11 q23. The use includes a compound of any of the Formulae disclosed herein for administration to a subject in need thereof in a therapeutically effective amount.

The present invention provides use of the compounds disclosed herein in preparation of a medicament for treating or preventing a disease or disorder in which DOT1L-mediated protein methylation plays a part or a disease or disorder mediated by DOT1L-mediated protein methylation. The use includes a compound of any of the Formulae disclosed herein for administration to a subject in need thereof in a therapeutically effective amount.

The present invention provides use of the compounds disclosed herein for inhibiting DOT activity in a cell. The use includes contacting the cell with an effective amount of one or more of the compound of any of the Formulae disclosed herein.

Still another aspect of the invention relates to a use of the compounds disclosed herein for reducing the level of Histone H3 Lysine residue 79 (H3-K79) methylation in a cell. The use includes contacting a cell with a compound of the present invention. Such use can ameliorate any condition which is caused by or potentiated by the activity of DOT1L through H3-K79 methylation.

In the formulae presented herein, the variables can be selected from the respective groups of chemical moieties later defined in the detailed description.

In addition, the invention provides methods of synthesizing the foregoing compounds. Following synthesis, a therapeutically effective amount of one or more of the compounds can be formulated with a pharmaceutically acceptable carrier for administration to a mammal, particularly humans, for use in modulating an epigenetic enzyme. In certain embodiments, the compounds of the present invention are useful for treating, preventing, or reducing the risk of cancer or for the manufacture of a medicament for treating, preventing, or reducing the risk of cancer. Accordingly, the compounds or the formulations can be administered, for example, via oral, parenteral, otic, ophthalmic, nasal, or topical routes, to provide an effective amount of the compound to the mammal.

Compounds of the present invention that contain nitrogens can be converted to N-oxides by treatment with an oxidizing agent (e.g., 3-chloroperoxybenzoic acid (mCPBA) and/or hydrogen peroxides) to afford other compounds of the present invention. Thus, all shown and claimed nitrogen-containing compounds are considered, when allowed by valence and structure, to include both the compound as shown and its N-oxide derivative (which can be designated as N→O or N$^+$—O$^-$). Furthermore, in other instances, the nitrogens in the compounds of the present invention can be converted to N-hydroxy or N-alkoxy compounds. For example, N-hydroxy compounds can be prepared by oxidation of the parent amine by an oxidizing agent such as m-CPBA. All shown and claimed nitrogen-containing compounds are also considered, when allowed by valence and structure, to cover both the compound as shown and its N-hydroxy (i.e., N—OH) and N-alkoxy (i.e., N—OR, wherein R is substituted or unsubstituted $C_1$-$C_6$ alkyl, $C_1$-$C_6$ alkenyl, $C_1$-$C_6$ alkynyl, 3-14-membered carbocycle or 3-14-membered heterocycle) derivatives.

In the present specification, the structural formula of the compound represents a certain isomer for convenience in some cases, but the present invention includes all isomers, such as geometrical isomers, optical isomers based on an asymmetrical carbon, stereoisomers, tautomers, and the like. In addition, a crystal polymorphism may be present for the compounds represented by the formula. It is noted that any crystal form, crystal form mixture, or anhydride or hydrate thereof is included in the scope of the present invention. Furthermore, so-called metabolite which is produced by degradation of the present compound in vivo is included in the scope of the present invention.

"Isomerism" means compounds that have identical molecular formulae but differ in the sequence of bonding of their atoms or in the arrangement of their atoms in space. Isomers that differ in the arrangement of their atoms in space are termed "stereoisomers." Stereoisomers that are not mirror images of one another are termed "diastereoisomers," and stereoisomers that are non-superimposable mirror images of each other are termed "enantiomers" or sometimes optical isomers. A mixture containing equal amounts of individual enantiomeric forms of opposite chirality is termed a "racemic mixture."

A carbon atom bonded to four non-identical substituents is termed a "chiral center."

"Chiral isomer" means a compound with at least one chiral center. Compounds with more than one chiral center may exist either as an individual diastereomer or as a mixture of diastereomers, termed "diastereomeric mixture." When one chiral center is present, a stereoisomer may be characterized by the absolute configuration (R or S) of that chiral center. Absolute configuration refers to the arrangement in space of the substituents attached to the chiral center. The substituents attached to the chiral center under consideration are ranked in accordance with the Sequence Rule of Cahn, Ingold and Prelog. (Cahn et al., *Angew. Chem. Inter. Edit.* 1966, 5, 385; errata 511; Cahn et al., *Angew. Chem.* 1966, 78, 413; Cahn and Ingold, *J. Chem. Soc.* 1951 (London), 612; Cahn et al., *Experientia* 1956, 12, 81; Cahn, *J. Chem. Educ.* 1964, 41, 116).

"Geometric isomer" means the diastereomers that owe their existence to hindered rotation about double bonds or a cycloalkyl linker (e.g., 1,3-cylcobutyl). These configurations are differentiated in their names by the prefixes cis and trans, or Z and E, which indicate that the groups are on the same or opposite side of the double bond in the molecule according to the Cahn-Ingold-Prelog rules.

It is to be understood that the compounds of the present invention may be depicted as different chiral isomers or geometric isomers. It should also be understood that when compounds have chiral isomeric or geometric isomeric forms, all isomeric forms are intended to be included in the scope of the present invention, and the naming of the compounds does not exclude any isomeric forms.

Furthermore, the structures and other compounds discussed in this invention include all atropic isomers thereof "Atropic isomers" are a type of stereoisomer in which the atoms of two isomers are arranged differently in space. Atropic isomers owe their existence to a restricted rotation caused by hindrance of rotation of large groups about a central bond. Such atropic isomers typically exist as a mixture, however as a result of recent advances in chromatography techniques, it has been possible to separate mixtures of two atropic isomers in select cases.

"Tautomer" is one of two or more structural isomers that exist in equilibrium and is readily converted from one isomeric form to another. This conversion results in the formal migration of a hydrogen atom accompanied by a switch of adjacent conjugated double bonds. Tautomers exist as a mixture of a tautomeric set in solution. In solutions where tautomerization is possible, a chemical equilibrium of the tautomers will be reached. The exact ratio of the tautomers depends on several factors, including temperature, solvent and pH. The concept of tautomers that are interconvertable by tautomerizations is called tautomerism.

Of the various types of tautomerism that are possible, two are commonly observed. In keto-enol tautomerism a simultaneous shift of electrons and a hydrogen atom occurs. Ring-chain tautomerism arises as a result of the aldehyde group (—CHO) in a sugar chain molecule reacting with one of the hydroxy groups (—OH) in the same molecule to give it a cyclic (ring-shaped) form as exhibited by glucose.

Common tautomeric pairs are: ketone-enol, amide-nitrile, lactam-lactim, amide-imidic acid tautomerism in heterocyclic rings (e.g., in nucleobases such as guanine, thymine and cytosine), amine-enamine and enamine-enamine. Benzimidazoles also exhibit tautomerism, when the benzimidazole contains one or more substituents in the 4, 5, 6 or 7 positions, the possibility of different isomers arises. For example, 2,5-dimethyl-1H-benzo[d]imidazole can exist in equilibrium with its isomer 2,6-dimethyl-1H-benzo[d]imidazole via tautomerization.

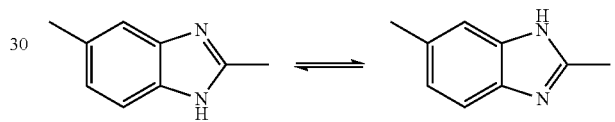

2,5-dimethyl-1H-benzo[d]imidazole  2,6-dimethyl-1H-benzo[d]imidazole

Another example of tautomerism is shown below.

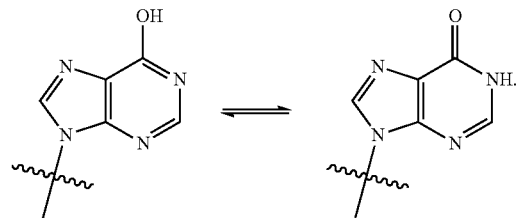 [SMILES: *n1cnc2c(O)ncnc21 ; *n1cnc2c(=O)[nH]cnc21]

It is to be understood that the compounds of the present invention may be depicted as different tautomers. It should also be understood that when compounds have tautomeric forms, all tautomeric forms are intended to be included in the scope of the present invention, and the naming of the compounds does not exclude any tautomer form.

The term "crystal polymorphs", "polymorphs" or "crystal forms" means crystal structures in which a compound (or a salt or solvate thereof) can crystallize in different crystal packing arrangements, all of which have the same elemental composition. Different crystal forms usually have different X-ray diffraction patterns, infrared spectral, melting points, density hardness, crystal shape, optical and electrical properties, stability and solubility. Recrystallization solvent, rate of crystallization, storage temperature, and other factors may cause one crystal form to dominate. Crystal polymorphs of the compounds can be prepared by crystallization under different conditions.

Compounds of the invention may be crystalline, semi-crystalline, non-crystalline, amorphous, mesomorphous, etc.

The compounds of any of the Formulae disclosed herein include the compounds themselves, as well as their N-oxides, salts, their solvates, and their prodrugs, if applicable. A salt, for example, can be formed between an anion and a positively charged group (e.g., amino) on the compound or inhibitor (e.g., a substituted nucleoside compound such as a substituted purine or 7-deazapurine compound). Suitable anions include chloride, bromide, iodide, sulfate, bisulfate, sulfamate, nitrate, phosphate, citrate, methanesulfonate, trifluoroacetate, glutamate, glucuronate, glutarate, malate, maleate, succinate, fumarate, tartrate, tosylate, salicylate, lactate, naphthalenesulfonate, and acetate. Likewise, a salt can also be formed between a cation and a negatively charged group (e.g., carboxylate) on the compound or inhibitor (e.g., a substituted nucleoside compound such as a substituted purine or 7-deazapurine compound). Suitable cations include sodium ion, potassium ion, magnesium ion, calcium ion, and an ammonium cation such as tetramethylammonium ion. The compound or inhibitor (e.g., a substituted nucleoside compound such as a substituted purine or 7-deazapurine compound) also include those salts containing quaternary nitrogen atoms. Examples of prodrugs include esters and other pharmaceutically acceptable derivatives, which, upon administration to a subject, are capable of providing active substituted nucleoside compound such as a substituted purine or 7-deazapurine.

Additionally, the compounds of the present invention, for example, the salts of the compounds, can exist in either hydrated or unhydrated (the anhydrous) form or as solvates with other solvent molecules. Nonlimiting examples of hydrates include hemihydrates, monohydrates, dihydrates, trihydrates, etc. Nonlimiting examples of solvates include ethanol solvates, acetone solvates, etc.

"Solvate" means solvent addition forms that contain either stoichiometric or non-stoichiometric amounts of solvent. Some compounds have a tendency to trap a fixed molar ratio of solvent molecules in the crystalline solid state, thus forming a solvate. If the solvent is water the solvate formed is a hydrate; and if the solvent is alcohol, the solvate formed is an alcoholate. Hydrates are formed by the combination of one or more molecules of water with one molecule of the substance in which the water retains its molecular state as $H_2O$. A hemihydrate is formed by the combination of one molecule of water with more than one molecule of the substance in which the water retains its molecular state as $H_2O$.

As used herein, the term "analog" refers to a chemical compound that is structurally similar to another but differs slightly in composition (as in the replacement of one atom by an atom of a different element or in the presence of a particular functional group, or the replacement of one functional group by another functional group). Thus, an analog is a compound that is similar or comparable in function and appearance, but not in structure or origin to the reference compound.

As defined herein, the term "derivative" refers to compounds that have a common core structure, and are substituted with various groups as described herein. For example, all of the compounds represented by Formula (I) are substituted purine compounds or substituted 7-deazapurine compounds, and have Formula (I) as a common core.

The term "bioisostere" refers to a compound resulting from the exchange of an atom or of a group of atoms with another, broadly similar, atom or group of atoms. The objective of a bioisosteric replacement is to create a new compound with similar biological properties to the parent compound. The bioisosteric replacement may be physico-chemically or topologically based. Examples of carboxylic acid bioisosteres include, but are not limited to, acyl sulfonimides, tetrazoles, sulfonates and phosphonates. See, e.g., Patani and LaVoie, *Chem. Rev.* 96, 3147-3176, 1996.

The present invention is intended to include all isotopes of atoms occurring in the present compounds. Isotopes include those atoms having the same atomic number but different mass numbers. By way of general example and without limitation, isotopes of hydrogen include tritium and deuterium, and isotopes of carbon include C-13 and C-14.

The present invention also provides methods for the synthesis of the compounds of any of the Formulae disclosed herein. The present invention also provides detailed methods for the synthesis of various disclosed compounds of the present invention according to the schemes and the Examples described in WO2012/075381, WO2012/075492, WO2012/082436, WO2012/75500, WO2014/026198, WO2014/035140, and US2014/0100184, the contents of each of which are hereby incorporated by reference in their entireties.

Throughout the description, where compositions are described as having, including, or comprising specific components, it is contemplated that compositions also consist essentially of, or consist of, the recited components. Similarly, where methods or processes are described as having, including, or comprising specific process steps, the processes also consist essentially of, or consist of, the recited processing steps. Further, it should be understood that the order of steps or order for performing certain actions is immaterial so long as the invention remains operable. Moreover, two or more steps or actions can be conducted simultaneously.

The synthetic processes of the invention can tolerate a wide variety of functional groups, therefore various substituted starting materials can be used. The processes generally provide the desired final compound at or near the end of the overall process, although it may be desirable in certain instances to further convert the compound to a pharmaceutically acceptable salt, ester, or prodrug thereof.

Compounds of the present invention can be prepared in a variety of ways using commercially available starting materials, compounds known in the literature, or from readily prepared intermediates, by employing standard synthetic methods and procedures either known to those skilled in the art, or which will be apparent to the skilled artisan in light of the teachings herein. Standard synthetic methods and procedures for the preparation of organic molecules and functional group transformations and manipulations can be obtained from the relevant scientific literature or from standard textbooks in the field. Although not limited to any one or several sources, classic texts such as Smith, M. B., March, J., *March's Advanced Organic Chemistry: Reactions, Mechanisms, and Structure*, 5$^{th}$ edition, John Wiley & Sons: New York, 2001; Greene, T. W., Wuts, P. G. M., *Protective Groups in Organic Synthesis*, 3$^{rd}$ edition, John Wiley & Sons: New York, 1999; R. Larock, *Comprehensive Organic Transformations*, VCH Publishers (1989); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995), incorporated by reference herein, are useful and recognized reference textbooks of organic synthesis known to those in the art.

Compounds suitable for the methods of the invention, once produced, can be characterized using a variety of assays known to those skilled in the art to determine whether the compounds have biological activity. For example, the molecules can be characterized by conventional assays, including but not limited to those assays described below, to determine whether they have a predicted activity, binding activity and/or binding specificity.

Furthermore, high-throughput screening can be used to speed up analysis using such assays. As a result, it can be possible to rapidly screen the molecules described herein for activity, using techniques known in the art. General methodologies for performing high-throughput screening are described, for example, in Devlin (1998) High Throughput Screening, Marcel Dekker; and U.S. Pat. No. 5,763,263. High-throughput assays can use one or more different assay techniques including, but not limited to, those described herein.

To further assess a compound's drug-like properties, measurements of inhibition of cytochrome P450 enzymes and phase II metabolizing enzyme activity can also be measured either using recombinant human enzyme systems or more complex systems like human liver microsomes. Further, compounds can be assessed as substrates of these metabolic enzyme activities as well. These activities are useful in determining the potential of a compound to cause drug-drug interactions or generate metabolites that retain or have no useful antimicrobial activity.

To get an estimate of the potential of the compound to be orally bioavailable, one can also perform solubility and Caco-2 assays. The latter is a cell line from human epithelium that allows measurement of drug uptake and passage through a Caco-2 cell monolayer often growing within wells of a 24-well microtiter plate equipped with a 1 micron membrane. Free drug concentrations can be measured on the basolateral side of the monolayer, assessing the amount of drug that can pass through the intestinal monolayer. Appropriate controls to ensure monolayer integrity and tightness of gap junctions are needed. Using this same system one can get an estimate of P-glycoprotein mediated efflux. P-glycoprotein is a pump that localizes to the apical membrane of cells, forming polarized monolayers. This pump can abrogate the active or passive uptake across the Caco-2 cell membrane, resulting in less drug passing through the intestinal epithelial layer. These results are often done in conjunction with solubility measurements and both of these factors are known to contribute to oral bioavailability in mammals. Measurements of oral bioavailability in animals and ultimately in man using traditional pharmacokinetic experiments will determine the absolute oral bioavailability.

Experimental results can also be used to build models that help predict physical-chemical parameters that contribute to drug-like properties. When such a model is verified, experimental methodology can be reduced, with increased reliance on the model predictability.

The present invention also provides pharmaceutical compositions comprising a compound of any of the Formulae disclosed herein in combination with at least one pharmaceutically acceptable excipient or carrier.

A "pharmaceutical composition" is a formulation containing the compounds of the present invention in a form suitable for administration to a subject. In one embodiment, the pharmaceutical composition is in bulk or in unit dosage form. The unit dosage form is any of a variety of forms, including, for example, a capsule, an IV bag, a tablet, a single pump on an aerosol inhaler or a vial. The quantity of active ingredient (e.g., a formulation of the disclosed compound or salt, hydrate, solvate or isomer thereof) in a unit dose of composition is an effective amount and is varied according to the particular treatment involved. One skilled in the art will appreciate that it is sometimes necessary to make routine variations to the dosage depending on the age and condition of the patient. The dosage will also depend on the route of administration. A variety of routes are contemplated, including oral, pulmonary, rectal, parenteral, transdermal, subcutaneous, intravenous, intramuscular, intraperitoneal, inhalational, buccal, sublingual, intrapleural, intrathecal, intranasal, and the like. Dosage forms for the topical or transdermal administration of a compound of this invention include powders, sprays, ointments, pastes, creams, lotions, gels, solutions, patches and inhalants. In one embodiment, the active compound is mixed under sterile conditions with a pharmaceutically acceptable carrier, and with any preservatives, buffers, or propellants that are required.

As used herein, the phrase "pharmaceutically acceptable" refers to those compounds, materials, compositions, carriers, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

"Pharmaceutically acceptable excipient" means an excipient that is useful in preparing a pharmaceutical composition that is generally safe, non-toxic and neither biologically nor otherwise undesirable, and includes excipient that is acceptable for veterinary use as well as human pharmaceutical use. A "pharmaceutically acceptable excipient" as used in the specification and claims includes both one and more than one such excipient.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), and transmucosal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

A compound or pharmaceutical composition of the invention can be administered to a subject in many of the well-known methods currently used for chemotherapeutic treatment. For example, for treatment of cancers, a compound of the invention may be injected directly into tumors, injected into the blood stream or body cavities or taken orally or applied through the skin with patches. The dose chosen should be sufficient to constitute effective treatment but not as high as to cause unacceptable side effects. The state of the disease condition (e.g., cancer, precancer, and the like) and the health of the patient should preferably be closely monitored during and for a reasonable period after treatment.

The term "therapeutically effective amount", as used herein, refers to an amount of a pharmaceutical agent to treat, ameliorate, or prevent an identified disease or condition, or to exhibit a detectable therapeutic or inhibitory effect. The effect can be detected by any assay method known in the art. The precise effective amount for a subject will depend upon the subject's body weight, size, and health; the nature and extent of the condition; and the therapeutic selected for administration. Therapeutically effective amounts for a given situation can be determined by routine experimentation that is within the skill and judgment of the clinician. In a preferred aspect, the disease or condition to be treated is cancer. In another aspect, the disease or condition to be treated is a cell proliferative disorder.

For any compound, the therapeutically effective amount can be estimated initially either in cell culture assays, e.g., of neoplastic cells, or in animal models, usually rats, mice, rabbits, dogs, or pigs. The animal model may also be used to determine the appropriate concentration range and route of administration. Such information can then be used to determine useful doses and routes for administration in humans. Therapeutic/prophylactic efficacy and toxicity may be determined by standard pharmaceutical procedures in cell cultures or experimental animals, e.g., $ED_{50}$ (the dose therapeutically effective in 50% of the population) and $LD_{50}$ (the dose lethal to 50% of the population). The dose ratio between toxic and therapeutic effects is the therapeutic index, and it can be expressed as the ratio, $LD_{50}/ED_{50}$. Pharmaceutical compositions that exhibit large therapeutic indices are preferred. The dosage may vary within this range depending upon the dosage form employed, sensitivity of the patient, and the route of administration.

Dosage and administration are adjusted to provide sufficient levels of the active agent(s) or to maintain the desired effect. Factors which may be taken into account include the severity of the disease state, general health of the subject, age, weight, and gender of the subject, diet, time and frequency of administration, drug interaction(s), reaction sensitivities, and tolerance/response to therapy. Long-acting pharmaceutical compositions may be administered every 3 to 4 days, every week, or once every two weeks depending on half-life and clearance rate of the particular formulation.

The pharmaceutical compositions containing active compounds of the present invention may be manufactured in a manner that is generally known, e.g., by means of conventional mixing, dissolving, granulating, dragee-making, levigating, emulsifying, encapsulating, entrapping, or lyophilizing processes. Pharmaceutical compositions may be formulated in a conventional manner using one or more pharmaceutically acceptable carriers comprising excipients and/or auxiliaries that facilitate processing of the active compounds into preparations that can be used pharmaceutically. Of course, the appropriate formulation is dependent upon the route of administration chosen.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol and sorbitol, and sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible pharmaceutically acceptable carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser, which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The active compounds can be prepared with pharmaceutically acceptable carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved.

In therapeutic applications, the dosages of the pharmaceutical compositions used in accordance with the invention vary depending on the agent, the age, weight, and clinical condition of the recipient patient, and the experience and judgment of the clinician or practitioner administering the therapy, among other factors affecting the selected dosage. Generally, the dose should be sufficient to result in slowing, and preferably regressing, the growth of the tumors and also preferably causing complete regression of the cancer. An effective amount of a pharmaceutical agent is that which provides an objectively identifiable improvement as noted by the clinician or other qualified observer. For example, regression of a tumor in a patient may be measured with reference to the diameter of a tumor. Decrease in the diameter of a tumor indicates regression. Regression is also indicated by failure of tumors to reoccur after treatment has stopped. As used herein, the term "dosage effective manner" refers to amount of an active compound to produce the desired biological effect in a subject or cell.

The pharmaceutical compositions can be included in a container, pack, or dispenser together with instructions for administration.

The compounds of the present invention are capable of further forming salts. All of these forms are also contemplated within the scope of the claimed invention.

As used herein, "pharmaceutically acceptable salts" refer to derivatives of the compounds of the present invention wherein the parent compound is modified by making acid or base salts thereof. Examples of pharmaceutically acceptable salts include, but are not limited to, mineral or organic acid salts of basic residues such as amines, alkali or organic salts of acidic residues such as carboxylic acids, and the like. The pharmaceutically acceptable salts include the conventional non-toxic salts or the quaternary ammonium salts of the parent compound formed, for example, from non-toxic inorganic or organic acids. For example, such conventional non-toxic salts include, but are not limited to, those derived from inorganic and organic acids selected from 2-acetoxybenzoic, 2-hydroxyethane sulfonic, acetic, ascorbic, benzene sulfonic, benzoic, bicarbonic, carbonic, citric, edetic, ethane disulfonic, 1,2-ethane sulfonic, fumaric, glucoheptonic, gluconic, glutamic, glycolic, glycollyarsanilic, hexylresorcinic, hydrabamic, hydrobromic, hydrochloric, hydroiodic, hydroxymaleic, hydroxynaphthoic, isethionic, lactic, lactobionic, lauryl sulfonic, maleic, malic, mandelic, methane sulfonic, napsylic, nitric, oxalic, pamoic, pantothenic, phenylacetic, phosphoric, polygalacturonic, propionic, salicyclic, stearic, subacetic, succinic, sulfamic, sulfanilic, sulfuric, tannic, tartaric, toluene sulfonic, and the commonly occurring amine acids, e.g., glycine, alanine, phenylalanine, arginine, etc.

Other examples of pharmaceutically acceptable salts include hexanoic acid, cyclopentane propionic acid, pyruvic acid, malonic acid, 3-(4-hydroxybenzoyl)benzoic acid, cinnamic acid, 4-chlorobenzenesulfonic acid, 2-naphthalenesulfonic acid, 4-toluenesulfonic acid, camphorsulfonic acid, 4-methylbicyclo-[2.2.2]-oct-2-ene-1-carboxylic acid, 3-phenylpropionic acid, trimethylacetic acid, tertiary butylacetic acid, muconic acid, and the like. The present invention also encompasses salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

It should be understood that all references to pharmaceutically acceptable salts include solvent addition forms (solvates) or crystal forms (polymorphs) as defined herein, of the same salt.

The compounds of the present invention can also be prepared as esters, for example, pharmaceutically acceptable esters. For example, a carboxylic acid function group in a compound can be converted to its corresponding ester, e.g., a methyl, ethyl or other ester. Also, an alcohol group in a compound can be converted to its corresponding ester, e.g., acetate, propionate or other ester.

The compounds of the present invention can also be prepared as prodrugs, for example, pharmaceutically acceptable prodrugs. The terms "pro-drug" and "prodrug" are used interchangeably herein and refer to any compound which releases an active parent drug in vivo. Since prodrugs are known to enhance numerous desirable qualities of pharmaceuticals (e.g., solubility, bioavailability, manufacturing, etc.), the compounds of the present invention can be delivered in prodrug form. Thus, the present invention is intended to cover prodrugs of the presently claimed compounds, methods of delivering the same and compositions containing the same. "Prodrugs" are intended to include any covalently bonded carriers that release an active parent drug of the present invention in vivo when such prodrug is administered to a subject. Prodrugs in the present invention are prepared by modifying functional groups present in the compound in such a way that the modifications are cleaved, either in routine manipulation or in vivo, to the parent compound. Prodrugs include compounds of the present invention wherein a hydroxy, amino, sulfhydryl, carboxy or carbonyl group is bonded to any group that may be cleaved in vivo to form a free hydroxyl, free amino, free sulfhydryl, free carboxy or free carbonyl group, respectively.

Examples of prodrugs include, but are not limited to, esters (e.g., acetate, dialkylaminoacetates, formates, phosphates, sulfates and benzoate derivatives) and carbamates (e.g., N,N-dimethylaminocarbonyl) of hydroxy functional groups, esters (e.g., ethyl esters, morpholinoethanol esters) of carboxyl functional groups, N-acyl derivatives (e.g., N-acetyl) N-Mannich bases, Schiff bases and enaminones of amino functional groups, oximes, acetals, ketals and enol esters of ketone and aldehyde functional groups in compounds of the invention, and the like, See Bundegaard, H., *Design of Prodrugs*, p 1-92, Elesevier, New York-Oxford (1985).

The compounds, or pharmaceutically acceptable salts, esters or prodrugs thereof, are administered orally, nasally, transdermally, pulmonary, inhalationally, buccally, sublingually, intraperintoneally, subcutaneously, intramuscularly, intravenously, rectally, intrapleurally, intrathecally and parenterally. In one embodiment, the compound is administered orally. One skilled in the art will recognize the advantages of certain routes of administration.

The dosage regimen utilizing the compounds is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter, or arrest the progress of the condition.

Techniques for formulation and administration of the disclosed compounds of the invention can be found in *Remington: the Science and Practice of Pharmacy*, 19$^{th}$ edition, Mack Publishing Co., Easton, Pa. (1995). In an embodiment, the compounds described herein, and the pharmaceutically acceptable salts thereof, are used in pharmaceutical preparations in combination with a pharmaceutically acceptable carrier or diluent. Suitable pharmaceutically acceptable carriers include inert solid fillers or diluents and sterile aqueous or organic solutions. The compounds will be present in such pharmaceutical compositions in amounts sufficient to provide the desired dosage amount in the range described herein.

All percentages and ratios used herein, unless otherwise indicated, are by weight. Other features and advantages of the present invention are apparent from the different examples. The provided examples illustrate different components and methodology useful in practicing the present invention. The examples do not limit the claimed invention. Based on the present disclosure the skilled artisan can identify and employ other components and methodology useful for practicing the present invention.

In the synthetic schemes described herein, compounds may be drawn with one particular configuration for simplicity. Such particular configurations are not to be construed as limiting the invention to one or another isomer, tautomer, regioisomer or stereoisomer, nor does it exclude mixtures of isomers, tautomers, regioisomers or stereoisomers.

Compounds described herein are assayed for modulation of activity, for example, histone methylation, modulation of cell growth and/or $IC_{50}$, described in the examples below. $IC_{50}$ values for DOT1L inhibition for select DOT1L inhibitors were determined as described in Example 1 and are listed below.

| Compound | DOT1L $IC_{50}$ (μM) |
|---|---|
| A2 | 0.00074 |

All publications and patent documents cited herein are incorporated herein by reference as if each such publication or document was specifically and individually indicated to be incorporated herein by reference. Citation of publications and patent documents is not intended as an admission that any is pertinent prior art, nor does it constitute any admission as to the contents or date of the same. The invention having now been described by way of written description, those of skill in the art will recognize that the invention can be practiced in a variety of embodiments and that the foregoing description and examples below are for purposes of illustration and not limitation of the claims that follow.

Example 1: General Methods

Cell Culture:

Human leukemia cell line EOL-1 (Catalog # ACC-386) was purchased from DSMZ and were grown in Roswell Park Memorial Institute medium (RPMI) with 10% Fetal Bovine Serum (FBS). Cells were kept in log growth as outlined in the technical data sheet provided by the vendor.

Cell Growth and Viability Assay

Exponentially growing EOL-1 cells were plated in 96-well plates at a density of $3 \times 10^4$ viable cells/well. Each treatment was seeded in triplicate with a final well volume of 150 μLs. Cells were incubated with increasing concentrations of DOT1L inhibitor up to 50 μM. Viable cell number was determined every 3-4 days for 11 days using the Guava Viacount assay (Millipore #4000-0040) and analyzed on a Guava EasyCyte Plus instrument according to the manufacturer's protocol. On the days of cell counts, growth media and inhibitor were replenished and cells maintained in log phase culture by reseeding at a density of $5 \times 10^4$ viable cells/well. Total cell number was expressed as split-adjusted viable cells per well. For each cell inhibitor $IC_{50}$ values were determined from concentration-dependence curves at day 11. All calculations were done using GraphPad Prism, version 5.00 for Windows, GraphPad Software, San Diego Calif. USA (www.graphpad.com).

Histone Extraction of Cell Pellets:

Frozen pellets were allowed to thaw briefly on ice and then lysed by a 5 minute incubation on ice with 250 μl nuclear extraction buffer (10 mM Tris-HCl, pH 7.6, 10 mM $MgCl_2$, 25 mM KCl, 1% Triton X-100, 8.6% Sucrose, plus a Roche protease inhibitor tablet 1836153001). Nuclei were collected by centrifugation at 600 g for 5 minutes at 4° C. and washed once in Tris/EDTA buffer (pH 7.4). Supernatant was removed and histones extracted for one hour with 60 μl 0.4 N cold sulfuric acid. Extracts were clarified by centrifugation at 10,000 g for 10 minutes at 4° C. and transferred to a fresh microcentrifuge tube containing 600 μl ice cold acetone. Histones were precipitated at −20° C. for 2 hours, pelleted by centrifugation at 10,000 g for 10 minutes and resuspended in 60 μl distilled water (DI water). Total protein of the acid extracts was assessed using a bicinchoninic acid (BCA) protein quantification assay with a bovine serum albumin (BSA) standard (Pierce Biotechnology).

H3K79me2 Immunoblot:

For immunoblot analysis of the H3K79me2 inhibition by DOT1L inhibitor, exponentially growing EOL-1 cells were seeded at $2 \times 10^5$ cells/mL and incubated in the presence of increasing concentrations of DOT1L inhibitor for 4 days. Following incubation, cells ($2-3 \times 10^6$) were harvested and histones extracted as described. Histones (400 ng) were fractionated on a 10-20% Tris HCl gels (Bio-Rad) with Tris-Glycine SDS running buffer (Invitrogen) under denaturing conditions and transferred to a nitrocellulose filter. The filter was incubated for 1 hour in blocking buffer (Odyssey blocking buffer, Li-cor, 927-40000) at RT and then incubated overnight at 4° C. in blocking buffer containing an antibody specific for H3K79me2 (1:5000 dilution, abcam ab3594). Filters were washed 3 times for 5 minutes with wash buffer (PBST) and incubated with infrared tagged secondary antibody (Alexa Flour 680 goat anti-rabbit IgG (1:20,000), Invitrogen A-21076) at RT for 1 hour. Filters were washed in PBST and reprobed for 1 hour at RT with the appropriate total histone antibody control (mouse anti-histone H3 (1:20,000), CST 3638, or mouse anti-histone H4 (1:10,000), CST 2935). Filters were washed again in PBST and incubated with infrared tagged secondary antibody (IRDye 800Cw donkey-anti-mouse IgG (1:20,000), Li-Cor 926-32212) at RT for 1 hour. After a final wash in PBST, filters were scanned using the Odyssey infrared imager (Li-cor). Signal intensities specific for each methyl-specific antibody was quantified using Odyssey software and normalized to that of the appropriate total histone control signal on the same filter by dividing the methyl-specific antibody signal intensity by the total histone control signal intensity.

Quantitative Real-Time PCR:

Exponentially growing EOL-1 cells were plated in a 12 well plate at $2 \times 10^5$ cells/mL. Cells were incubated in the presence of increasing concentrations of EPZ-5676 up to 10 µM. On day 4, cells were maintained in log phase culture by reseeding at $5 \times 10^5$ cells/mL and compound was replenished. At day 6 cells were washed twice with PBS and pelleted by centrifugation at 200×g. Cell pellets were lysed in 300 µL RLT buffer (Qiagen) and total RNA was isolated using the RNeasy total RNA isolation kit (Qiagen 74106). Total RNA (1 µg) was reverse transcribed using a high capacity cDNA reverse transcription kit (Applied Biosystems 4368813). RNA isolation and cDNA synthesis were carried out according to the manufacturer's protocol. Predesigned labeled primer and probe sets for HOXA9 (Hs00365956), MEIS1 (Hs00180020) and FLT3 (Hs00975659) were purchased from Applied Biosystems. Quantitative real-time PCR (qPCR) reactions contained 50 ng cDNA, 1× labeled primer and probe set, and 1× Taqman universal PCR master mix (Applied Biosystems 4304437). Samples were run on a 7900 HT Fast Real Time PCR machine (Applied Biosystems 4351405) with cycling conditions of 2 min 50° C., 10 min 95° C., 40 cycles at 15 sec 95° C. and 1 min 60° C. Target gene cycle numbers were normalized to the house keeping gene β2-microglobulin (Applied Biosystems 4333766) to get a ΔCT value. Percent of DMSO control was calculated with the equation $(2^{-\Delta\Delta CT})*100$ where the ΔΔCT is the difference between normalized target gene and DMSO control (ΔCT sample−ΔCT control=ΔΔCT).

Determination of $IC_{50}$.

Test compounds were serially diluted 3 fold in DMSO for 10 points and 1 µl was plated in a 384 well microtiter plate. Positive control (100% inhibition standard) was 2.5 uM final concentration of S-adenosyl-L-homocysteine and negative control (0% inhibition standard) contained 1 µl of DMSO. Compound was then incubated for 30 minutes with 40 µl per well of DOT1L (1-416) (0.25 nM final concentration in assay buffer: 20 mM TRIS, pH 8.0, 10 mM NaCl, 0.002% Tween20, 0.005% Bovine Skin Gelatin, 100 mM KCl, and 0.5 mM DTT). 10 µl per well of substrate mix (same assay buffer with 200 nM S-[methyl-$^3$H]-adenosyl-L methionine, 600 nM of unlabeled S-[methyl-$^3$H]-adenosyl-L methionine, and 20 nM oligonucleosome) was added to initiate the reaction. Reaction was incubated for 120 minutes at room temperature and quenched with 10 µl per well of 100 µM S-methyl-adenosyl-L methionine. For detection, substrate from 50 µl of reaction was immobilized on a 384 well Streptavidin coated Flashplate (Perkin Elmer) (also coated with 0.2% polyethyleneimine) and read on a Top Count scintillation counter (Perkin Elmer).

Other related general procedures and specific preparation procedures can also be found in the PCT publication Nos. WO2012/075381 and WO2014/026198, the contents of each are incorporated herein by reference in their entireties.

Results are shown in the accompanying Figures and Appendix 1 of U.S. Provisional Application Ser. No. 61/903,912 filed Nov. 13, 2013, the content of which is incorporated herein by reference in its entirety.

The expansion stage of a Phase 1 study is enrolling adult patients with MLL-r and MLL-PTD who are being treated with 90 mg/m$^2$/day with uninterrupted administration. The continued safety of the compound of Formula (I) or its N-oxide or a pharmaceutically acceptable salt thereof has been demonstrated, and there have been no drug-related treatment discontinuations in the study to date.

A Phase 1b study in pediatric patients with MLL-r leukemia is also ongoing. MLL-r comprises approximately 15% of pediatric acute leukemias and is considered to be the last remaining subtype of pediatric acute leukemia for which current treatment is inadequate. The pediatric Phase 1b study is designed to evaluate the safety, pharmacokinetics, and pharmacodynamics of escalating doses of the compound of Formula (I) or its N-oxide or a pharmaceutically acceptable salt thereof in patients between the ages of 3 months and 18 years and to also provide a preliminary assessment of efficacy. Doses start at 45 mg/m$^2$/day for patients younger than 12 months of age and at 70 mg/m$^2$/day for patients older than 12 months.

The entire disclosure of each of the patent documents and scientific articles referred to herein is incorporated by reference for all purposes.

The invention can be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes that come within the meaning and range of equivalency of the claims are intended to be embraced therein.

What is claimed is:

1. A method of treating leukemia comprising administering to a human pediatric subject in need thereof a therapeutically effective amount of a compound of Formula (I) or its N-oxide or a pharmaceutically acceptable salt thereof:

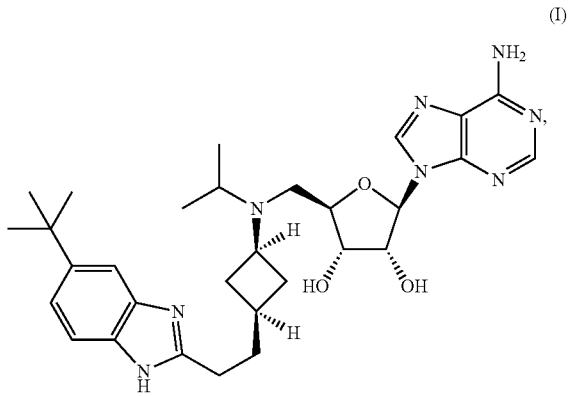 [SMILES: CC(C)N(C[C@H]1O[C@@H](n2cnc3c(N)ncnc32)[C@H](O)[C@@H]1O)[C@H]1C[C@@H](CCc2nc3cc(C(C)(C)C)ccc3[nH]2)C1]

(I)

at a dose of at least 45 mg/m$^2$/day for at least 7 days, wherein:

the human pediatric subject is 12 months or younger, and the compound of Formula (I) or its N-oxide or the pharmaceutically acceptable salt thereof is administered at a dose of about 45 mg/m$^2$/day, about 50 mg/m$^2$/day, about 55 mg/m$^2$/day, about 60 mg/m$^2$/day, about 65 mg/m$^2$/day, about 70 mg/m$^2$/day, about 75 mg/m²/day, about 80 mg/m²/day, about 85 mg/m²/day, about 90 mg/m²/day, about 95 mg/m²/day, or about 100 mg/m²/day; or the human pediatric subject is older than 12 months but younger than 18 months, and the compound of Formula (I) or its N-oxide or the pharmaceutically acceptable salt thereof is administered at a dose of about 70 mg/m²/day, about 75 mg/m²/day, about 80 mg/m²/day, about 85 mg/m²/day, about 90 mg/m²/day, about 95 mg/m²/day, or about 100 mg/m²/day.

2. The method of claim 1, wherein the compound of Formula (I) or its N-oxide or a pharmaceutically acceptable salt thereof is administered continuously without a drug holiday.

3. The method of claim 1, wherein the administration results in the reduction of H3K79 methyl mark to 90% or less, 80% or less, 70% or less, 60% or less, 50% or less, 40% or less, 30% or less, 20% or less, or 10% or less, of untreated control levels.

4. The method of claim 1, wherein the administration results in a suppression of H3K79 methyl mark rebound.

5. The method of claim 1, wherein the compound of Formula (I) or its N-oxide or a pharmaceutically acceptable salt thereof is administered for at least 14, 21, 28, 35, 42, 47, 56, or 64 days.

6. The method of claim 1, wherein the administration results in that at least 20%, at least 50%, or at least 80% of leukemic blast cells undergo maturation or differentiation.

7. The method of claim 1, wherein the administration results in that at least 20%, 30%, 40%, 50%, 60%, 70%, 80%, or 90% of the leukemic blast cells undergo cell death or apoptosis.

8. The method of claim 1, wherein the leukemia is chronic myelomonocytic leukemia (CMML), acute myeloid leukemia (AML) or leukemia characterized by MLL gene rearrangement.

9. The method of claim 8, wherein the MLL gene rearrangement is translocation of the MLL gene 11q23 or partial tandem duplication of the MLL gene, or the MLL gene rearrangement results in increased or errant DOT1L methylation activity.

10. The method of claim 8, wherein the method of treatment includes resolution of fevers, resolution of cachexia or resolution of leukemia cutis.

11. The method of claim 10, wherein the method of treatment results in restoration of normal haematopoiesis.

12. The method of claim 1, wherein the human pediatric subject is 12 months or younger, and the compound of Formula (I) or its N-oxide or the pharmaceutically acceptable salt thereof is administered at a dose of about 45 mg/m²/day, about 50 mg/m²/day, about 55 mg/m²/day, about 60 mg/m²/day, about 65 mg/m²/day, about 70 mg/m²/day, about 75 mg/m²/day, about 80 mg/m²/day, about 85 mg/m²/day, about 90 mg/m²/day, about 95 mg/m²/day, or about 100 mg/m²/day.

13. The method of claim 12, wherein the compound of Formula (I) or its N-oxide or a pharmaceutically acceptable salt thereof is administered continuously at a dose of 45 mg/m²/day without a drug holiday.

14. The method of claim 12, wherein the compound of Formula (I) or its N-oxide or a pharmaceutically acceptable salt thereof is administered at a dose of 45 mg/m²/day with a drug holiday.

15. The method of claim 14, wherein the compound of Formula (I) or its N-oxide or a pharmaceutically acceptable salt thereof is administered for 21 days of a 28-day cycle with a 7-day drug holiday.

16. The method of claim 1, wherein the human pediatric subject is older than 12 months but younger than 18 months, and the compound of Formula (I) or its N-oxide or a pharmaceutically acceptable salt thereof is administered at a dose of about 70 mg/m²/day, about 75 mg/m²/day, about 80 mg/m²/day, about 85 mg/m²/day, about 90 mg/m²/day, about 95 mg/m²/day, or about 100 mg/m²/day.

17. The method of claim 16, wherein the compound of Formula (I) or its N-oxide or a pharmaceutically acceptable salt thereof is administered continuously at a dose of 70 mg/m²/day without a drug holiday.

18. The method of claim 16, wherein the compound of Formula (I) or its N-oxide or a pharmaceutically acceptable salt thereof is administered at a dose of 70 mg/m²/day with a drug holiday.

19. The method of claim 18, wherein the compound of Formula (I) or its N-oxide or a pharmaceutically acceptable salt thereof is administered for 21 days of a 28-day cycle with a 7-day drug holiday.

* * * * *